US010463640B2

(12) United States Patent
Cohen et al.

(10) Patent No.: US 10,463,640 B2
(45) Date of Patent: *Nov. 5, 2019

(54) THERAPEUTIC APPROACHES FOR TREATING CMT AND RELATED DISORDERS

(71) Applicant: PHARNEXT, Issy-les-Moulineaux (FR)

(72) Inventors: Daniel Cohen, Saint Cloud (FR); Ilya Chumakov, Vaux le Penil (FR); Oxana Guerassimenko, Milly-la-Foret (FR); Serguei Nabirochkin, Chatenay Malabry (FR)

(73) Assignee: PHARNEXT, Issy-les-Moulineaux (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/055,797

(22) Filed: Aug. 6, 2018

(65) Prior Publication Data
US 2018/0338969 A1 Nov. 29, 2018

Related U.S. Application Data

(63) Continuation of application No. 15/966,848, filed on Apr. 30, 2018, now Pat. No. 10,322,101, which is a continuation of application No. 14/627,229, filed on Feb. 20, 2015, now abandoned, which is a continuation of application No. 12/744,962, filed as application No. PCT/EP2008/066468 on Nov. 28, 2008, now Pat. No. 8,992,891.

(60) Provisional application No. 60/991,800, filed on Dec. 3, 2007.

(30) Foreign Application Priority Data

Nov. 30, 2007 (EP) .................................. 07301614

(51) Int. Cl.
A61K 31/047 (2006.01)
A61P 25/02 (2006.01)
A61P 21/00 (2006.01)
A61K 31/197 (2006.01)
A61K 31/395 (2006.01)
A61K 31/485 (2006.01)
A61K 9/00 (2006.01)
A61K 9/08 (2006.01)
A61K 9/48 (2006.01)
A61K 31/7004 (2006.01)

(52) U.S. Cl.
CPC .......... A61K 31/197 (2013.01); A61K 9/0053 (2013.01); A61K 9/0095 (2013.01); A61K 9/08 (2013.01); A61K 9/4866 (2013.01); A61K 31/047 (2013.01); A61K 31/395 (2013.01); A61K 31/485 (2013.01); A61K 31/7004 (2013.01); A61P 25/02 (2018.01)

(58) Field of Classification Search
CPC ......... A61K 31/047; A61P 25/02; A61P 21/00
See application file for complete search history.

(56) References Cited

U.S. PATENT DOCUMENTS

| | | | |
|---|---|---|---|
| 7,592,372 B2 | 9/2009 | Osugi | |
| 8,716,269 B2* | 5/2014 | Cohen | A61K 31/197 514/171 |
| 8,992,891 B2* | 3/2015 | Cohen | A61K 31/197 424/49 |
| 9,393,241 B2* | 7/2016 | Cohen | A61K 31/436 |
| 9,427,436 B1* | 8/2016 | Cohen | A61K 31/192 |
| 9,566,275 B2* | 2/2017 | Cohen | A61K 31/436 |
| 2003/0069213 A1 | 4/2003 | Il et al. | |
| 2005/0038062 A1 | 2/2005 | Burns et al. | |
| 2005/0187290 A1 | 8/2005 | Fontes et al. | |
| 2005/0220863 A1 | 10/2005 | Han | |
| 2007/0099947 A1 | 5/2007 | Dean et al. | |
| 2007/0110801 A1 | 5/2007 | Perovitch et al. | |
| 2007/0299098 A1 | 12/2007 | Tanabe | |
| 2008/0206332 A1 | 8/2008 | Kidney et al. | |
| 2008/0255062 A1 | 10/2008 | Fernyhough et al. | |
| 2010/0310641 A1 | 12/2010 | Cohen et al. | |
| 2012/0040940 A1 | 2/2012 | Cohen et al. | |
| 2012/0088744 A1 | 4/2012 | Cohen et al. | |
| 2012/0270836 A1 | 10/2012 | Cohen et al. | |
| 2013/0059876 A1 | 3/2013 | Angeli | |
| 2013/0085122 A1 | 4/2013 | Cohen et al. | |
| 2013/0090307 A1 | 4/2013 | Cohen et al. | |
| 2015/0157626 A1 | 2/2015 | Cohen et al. | |
| 2016/0113867 A1 | 4/2016 | Cohen et al. | |
| 2017/0165256 A1 | 6/2017 | Cohen et al. | |

(Continued)

FOREIGN PATENT DOCUMENTS

| | | | |
|---|---|---|---|
| CA | 2727064 A1 | 12/2009 | |
| DE | 102006016990 A1 | 10/2007 | |
| EP | 0778023 | 6/1997 | |

(Continued)

OTHER PUBLICATIONS

Bassi et al., "Encephalomyelitis with Thyrotoxicosis," Journal of Neurology, vol. 218, No Month Listed 1978 (pp. 293-295).

(Continued)

*Primary Examiner* — Rachael E Bredefeld
*Assistant Examiner* — Chris E Simmons
(74) *Attorney, Agent, or Firm* — Andrea L. C. Reid; Dechert LLP

(57) ABSTRACT

Compositions and methods for the treatment of Charcot-Marie-Tooth disease and related disorders. Also provided are combination therapies for treating this disease by decreasing PMP22 expression in a subject.

9 Claims, 4 Drawing Sheets
Specification includes a Sequence Listing.

(56) References Cited

U.S. PATENT DOCUMENTS

2018/0000813 A1 1/2018 Cohen et al.

FOREIGN PATENT DOCUMENTS

| EP | 2065038 A1 | 6/2009 |
|---|---|---|
| EP | 2263665 A1 | 12/2010 |
| WO | 2000020024 A2 | 4/2000 |
| WO | 0249607 A2 | 6/2002 |
| WO | 2003077867 A2 | 9/2003 |
| WO | 2004006911 | 1/2004 |
| WO | 2004019938 A1 | 3/2004 |
| WO | 2004103263 A2 | 12/2004 |
| WO | 2005032555 A2 | 4/2005 |
| WO | 2005053612 A2 | 6/2005 |
| WO | 2006117573 | 11/2006 |
| WO | 2007134077 A2 | 11/2007 |
| WO | 2007134136 A2 | 11/2007 |
| WO | 2009068668 A1 | 6/2009 |
| WO | 2009153291 | 12/2009 |
| WO | 2010139627 A1 | 12/2010 |
| WO | 2011054759 | 5/2011 |
| WO | 2012117076 | 9/2012 |
| WO | 2014195394 A1 | 12/2014 |

OTHER PUBLICATIONS

Berenbaum et al., "Synergy, Additivism and Antagonism in Immunosuppression: A Critical Review," Clinical & Experimental Immunology, vol. 28, No Month Listed 1977 (pp. 1-18).

Bird, "Charcot-Marie-Tooth Neuropathy Type 1," GeneReviews—NCBI Bookshelf, 1998, pp. 1-41.

Chambliss, W.G., Sodium Acetate monograph in Handbook of Pharmaceutical Excipients, 5th ed., 2006, pp. 654-655.

Chemidex Pharma Ltd. "Lyflex 5mg/5ml Oral Solution" XP-002476376, retrieved from the Internet:http://emc.medicines.orq.uk/emc/assets/c/html/DisclavDoc.asp?documentID=14939, Apr. 14, 2008.

Cintas, P. et al. "Drug therapy for symptomatic relief in ALS-Quels sont les traitements medicamenteux syptomatiques?" Revue Neurologique, Jun. 1, 2006, pp. 4S235-4S243, vol. 162.

National Institute of Neurological Disorders and Stroke, "Charcot-Marie-Tooth Disease Fact Sheet," retrieved from the Internet: https://www.ninds.nih.gov/Disorders/Patient-caregiver-education/Fact-sheets/Charcot-Marie-Tooth-Disease-Fact-Sheet, Jan. 9, 2018.

Coffey et al., "Familial Trigeminal Neuralgia and Charcot-Marie-Tooth Neuropathy—Report of Two Families and Review," Surgical Neurology, vol. 35, Jan. 1, 1991 (pp. 49-53).

Colombo et al., "Effects of the Combination of Naltrexone and Baclofen on Acquisition of Alcohol Drinking Behavior in Alcohol-Preferring Rats," Drug and Alcohol Dependence, vol. 77, No. 1, No Month Listed 2005 (pp. 87-91).

Gabreëls-Festen et al., "Charcot-Marie-Tooth disease type 1A: morphological phenotype of the 17p duplication versus PMP22 point mutations," Acta Neuropathologica, vol. 90, 1995, pp. 645-649.

Gallagher, P. et al. "Persistent effects of mifepristone (RU-486) on cortisol levels in bipolar disorder and schizophrenia" Journal of Psychiatric Research, Oct. 1, 2008, pp. 1037-1041, vol. 42, No. 12.

Genetics Home Reference: Your Guide to Understanding Genetics Conditions. "Charcot-Marie-Tooth Disease," Dec. 11, 2012 <http://ghr.nlm.nih.gov/condition/charcot-marie-tooth-disease/show/print> (15 pages).

Gironi, M. et al. "A pilot trial of low-dose naltrexone in primary progressive multiple sclerosis" Multiple Sclerosis, Sep. 1, 2008, pp. 1076-1083, vol. 14, No. 8.

Graham et al., "A modified peripheral neuropathy scale: the Overall Neuropathy Limitations Scale," Journal of Neurology, Neurosurgery and Psychiatry, vol. 77, 2006, pp. 973-976.

Grandis et al., "Current Therapy for Charcot-Marie-Tooth Disease," Current Treatment Options in Neurology, vol. 7, No. 1, No Month Listed 2005 (pp. 23-31).

Haberlová et al., "Utility of Charcot-Marie-Tooth Neuropathy Score in children with type 1A disease," Pediatric Neurology, vol. 43, 2010, pp. 407-410.

Herrmann, D. N. et al. "Experimental Therapeutics in Hereditary Neuropathies: The Past, the Present and the Future" Neurotherapeutics, Jan. 1, 2008, pp. 507-515, vol. 5, No. 4.

International Search Report and Written Opinion issued by the European Patent Office as International Searching Authority for International Application No. PCT/EP2010/057438 dated Nov. 4, 2010 (19 pages).

International Search Report and Written Opinion issued by the European Patent Office as International Searching Authority for International Application No. PCT/EP2014/061664 dated Jun. 30, 2014 (10 pages).

International Search Report and Written Opinion issued by the European Patent Office as International Searching Authority for International Application No. PCT/EP2008/066468 dated Mar. 3, 2009 (14 pages).

Jones, D., Chapter 1: Pharmaceutical Solutions for Oral Administration. In Pharmaceutics—Dosage Form and Design, 1E (2008).

Keltner, J. L. "Myotonic Pupils in Charcot-Marie-Tooth Disease, Successful Relief of Symptoms with 0.025% Pilocarpine" Achieves of Ophthalmology, Jan. 1, 1975, pp. 1141-1148, vol. 93, No. 11.

Lees, A. J. et al. "Baclofen in Parkinson's disease" Journal of Neurology, Neurosurgery & Psychiatry, Jan. 1, 1978, pp. 707-708, vol. 41.

Li et al., "Effect of Baclofen Combined with Neural Facilitation Technique on the Reduction of Muscular Spasm in Patients with Spinal Cord Injury," Neural Regeneration Research, vol. 2, No. 8, Aug. 2007 (pp. 510-512).

Magnaghi et al., "GABA Receptor-Mediated Effects in the Peripheral Nervous System—A Cross-Interaction with Neuroactive Steroids," Journal of Molecular Neuroscience, vol. 28, No. 1, No Month Listed 2006 (pp. 89-102).

Maxwell et al., "Two rapid and simple methods used for the removal of resins from 1.0 micron thick epoxy sections," Journal of Microscopy, vol. 112, 1978, pp. 253-255.

Meyer Zu Horste et al., "Antiprogesterone Therapy Uncouples Axonal Loss from Demyelination in a Transgenic Rat Model of CMT1A Neuropathy," Annals of Neurology, vol. 61, 2007, pp. 61-72.

MHRA, "Baclofen 5MG/5ML Oral Solution," Retrieved from the Internet <http://www.mhra.gov.uk/home/groups/par/documents/websiteresources/con094157.pdf> Aug. 2, 2010 (22 pages).

Norris, F. H. et al. "Trial of Baclofen in Amyotrophic Lateral Sclerosis" Archives of Neurology, Nov. 1, 1979, pp. 715-716, vol. 36.

Pharminfotech, "Baclofen," Formulation in Pharmacy Practice—eMixt, Retrieved from the Internet <http://www.pharminfotech.co.nz/manual/Formulation/mixtures/baclofen.html> Aug. 31, 2011 (2 pages).

Pomara, N. et al. "Mifepristone (RU 486) for Alzheimer's disease" Neurology, May 1, 2002, p. 1436, vol. 58, No. 9.

RightDiagnosis.com http://www.rightdiagnosis.com/n/neuropathy/subtypes.htm. Accessed Feb. 28, 2014 (pp. 1-9).

Rivlin et al., "Objective clinical assessment of motor function after experimental spinal cord injury in the rat," Journal of Neurosurgery, vol. 47, 1977, pp. 577-581.

SciFinder® Sorbitol Search Results (2018). Copyright © 2018 American Chemical Society (ACS).

Sereda et al., "A transgenic rat model of Charcot-Marie-Tooth disease," Neuron, vol. 16, 1996, pp. 1049-1060.

Shy et al., "Reliability and validity of the CMT neuropathy score as a measure of disability," Neurology, vol. 64, 2005, pp. 1209-1214.

Slavik, J. et al. "In Vitro Correlates of in Vivo Rapamycin Therapy in Patients with Multiple Sclerosis" Clinical Immunology, Jan. 1, 2006, p. S113, vol. 119.

Stella et al., "Prodrug Strategies to Overcome Poor Water Solubility," Advanced Drug Delivery Reviews 59, No Month Listed 2007 (pp. 677-694).

(56) References Cited

OTHER PUBLICATIONS

Weimer et al., "Medication-Induced Exacerbation of Neuropathy in Charcot-Marie-Tooth Disease," Journal of Neurological Science, vol. 242, No. 1-2, No Month Listed 2006 (pp. 47-54).
Wilcock, G. K. et al. "A placebo-controlled, double-blind trial of the selective AB-42 lowering agent, flurizan (MPC-7869, (R)-flurbiprofen) in patients with mild to moderate Alzheimer's disease" Alzheimer's & Dementia: The Journal of the Alzheimer's Association, Jul. 1, 2005, p. S95, vol. 1, No. 1, Abstract Feb. 1, 2005.
Zu Horste, G. M. et al. "Myelin disorders: Causes and Perspectives of Charcot-Marie-Tooth Neuropathy" Journal of Molecular Neuroscience, Jan. 1, 2006, pp. 77-88, vol. 28, No. 1.
Garcia et al, (Neurology, 1998, 50, 1061-1067) (Year: 1998).
CMTPEDS (http://calculator.cmtpeds.org/ , 2015) (Year: 2018).

* cited by examiner

*:p<0.01; :p<0.001; *:p<0.0001: significatively different from control (no drug) Student's t test

SEQUENCE LISTING

```
<160> NUMBER OF SEQ ID NOS: 8

<210> SEQ ID NO 1
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1
ggaaacgcga atgaggc                                                      17

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
gttctgtttg gtttggctt                                                    19

<210> SEQ ID NO 3
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 3
```
ctgccctcaa ggttgtg                                                    17

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
cttcttcttc cggtaatgga t                                               21

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
gctctgagcg tgcatagggt ac                                              22

<210> SEQ ID NO 6
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 6
tcgggtggaa gtaccagcc                                                  19

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 7
agggagggag gaaggaaacc agaaa                                           25

<210> SEQ ID NO 8
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 8
tgacagctac tctggaggag aaacggaa                                        28

THERAPEUTIC APPROACHES FOR TREATING CMT AND RELATED DISORDERS

CROSS-REFERENCE TO RELATED APPLICATIONS

This application is a Continuation of U.S. application Ser. No. 15/966,848, filed on Apr. 30, 2018, which is a Continuation of U.S. application Ser. No. 14/627,229, filed on Feb. 20, 2015, which is a Continuation of U.S. application Ser. No. 12/744,962, filed on May 27, 2010, now U.S. Pat. No. 8,992,891, which is the National Stage of International Application No. PCT/EP2008/066468, filed on Nov. 28, 2008, which claims the benefit of U.S. Provisional Application No. 60/991,800, filed on Dec. 3, 2007, and priority to European Application No. 07301614.9, filed on Nov. 30, 2007. The content of the aforementioned applications is incorporated herein by reference in its entirety.

BACKGROUND

Field of the Invention

The present invention relates to compositions and methods for the treatment of the Charcot-Marie-Tooth disease and related disorders.

Background Information

Charcot-Marie-Tooth disease ("CMT") is an orphan genetic peripheral poly neuropathy. Affecting approximately 1 in 2,500 individuals, this disease is the most common inherited disorder of the peripheral nervous system. Its onset typically occurs during the first or second decade of life, although it may be detected in infancy. Course of disease is chronic with gradual neuromuscular degeneration. The disease is invalidating with cases of accompanying neurological pain and extreme muscular disability. CMT is one of the best studied genetic pathologies with approximately 30,000 cases in France. While a majority of CMT patients harbour a duplication of a chromosome 17 fragment containing a myelin gene: PMP22 (form CMT1A), two dozens of genes have been implicated in different forms of CMT. Accordingly, although monogenic in origin, this pathology manifests clinical heterogeneity due to possible modulator genes. The genes mutated in CMT patients are clustering around tightly connected molecular pathways affecting differentiation of Schwann cells or neurons or changing interplay of these cells in peripheral nerves.

PMP22 is a major component of myelin expressed in the compact portion of essentially all myelinated fibers in the peripheral nervous system and is produced predominantly by Schwann cells. A modest, 1.5-fold over expression of a normal PMP22 protein is also observed in Schwann cells heterozygous for the duplication in CMT patients (in some rare cases, CMT1A-like phenotype can be also linked to structural mutations in PMP22 protein) (Lupski et al., 1992; Suter et al., 1992; Roa et al., 1993; Thomas et al., 1997; Suter & Scherer, 2003; Nave & Sereda, 2007). Direct evidence that abnormal PMP22 gene dosage causes a CMT1A-like phenotype was provided by transgenic experiments in rodent models with over expression of PMP22 protein (Niemann et al., 1999; Perea et al., 2001; Robaglia-Schlupp et al., 2002; Meyer et al., 2006; Sereda & Nave, 2006). Furthermore, therapeutic interventions with onapristone: specific inhibitor of progesterone receptor (Sereda et al., 2003; Meyer zu Horste et al., 2007). and ascorbic acid (Passage et al., 2004) decreased this expression in the transgenic animals ameliorating or slowing the progression of disease phenotype.

Existing experimental data are indicating that PMP22 protein is not only the structural component of myelin sheaths, but also as an important regulatory protein, influencing multiple phenotypic traits in Schwann cells. The exact mechanism linking abnormal level of the protein to a modification of its functions in a mutant CMT1A glia cell is not completely understood, but some cellular mechanisms potentially explaining its detrimental effects on Schwann cell biology are starting to emerge.

Mining of publicly available data, describing molecular mechanisms and pathological manifestations of the CMT1A disease, allowed us to prioritize a few functional cellular modules—transcriptional regulation of PMP22 gene, PMP22 protein folding/degradation, Schwann cell proliferation and apoptosis, extra-cellular matrix deposition and remodelling, immune response—as potential legitimate targets for CMT-relevant therapeutic interventions. The combined impact of these deregulated functional modules on onset and progression of pathological manifestations of Charcot-Marie-Tooth justifies a potential efficacy of combinatorial CMT treatment.

The initial building of dynamic model of CMT pathology has been followed by a selection of marketed generic drugs targeting to functional regulation of CMT1A disease-relevant cellular pathways.

SUMMARY

The purpose of the present invention is to provide new therapeutic approaches for treating CMT and related disorders. The invention also relates to compositions and methods for modulation of PMP22 expression in a subject.

The inventors have identified various pathways which can be regulated in a subject to ameliorate CMT and related disorders. The inventors have also identified several drugs which, in combination(s) or alone, can effectively affect such pathways leading to CMT and related disorders, and represent new therapy for the treatment of these disorders.

The invention therefore provides novel compositions and methods for treating CMT disease and related disorders.

An object of this invention more specifically relates to the use of combinations of compounds for (the manufacture of a medicament for) treating CMT or a related disorder, wherein said compounds are selected from a GABA-B receptor agonist, a muscarinic receptor agonist, an antagonist of a steroid hormone receptor, a drug affecting the D-sorbitol signalling pathways, an opioid receptor antagonist, a thyroid hormone signalling inhibitor, an ERK (extracellular signal-regulated kinase) activator and a pAkt kinase inhibitor, a COX inhibitor, and any combination(s) thereof.

Another object of the invention relates to the use of combinations of compounds selected from: compound A: D-Sorbitol (CAS 50-70-4) and its possible salts, prodrugs and derivatives; compound B: Baclofen (CAS 1134-47-0 and CAS 63701-56-4 for baclofen-hydrochloride) and its possible salts, prodrugs and derivatives; compound C: Pilocarpine (CAS 92-13-7 and CAS 54-71-7 for pilocarpine hydrochloride) and its possible salts, prodrugs and derivatives; compound D: Naltrexone (CAS 16590-41-3 and CAS 16676-29-2 for naltrexone hydrochloride) and its possible salts, prodrugs and derivatives; compound E: Methimazole (CAS 60-56-0) and its possible salts and derivatives; compound F: Mifepristone (CAS 84371-65-3) and its possible salts, prodrugs and derivatives; Montelukast (CAS 158966-92-8) and its possible salts and derivatives; Ketoprofen (CAS 22071-15-4 and CAS 57495-14-4 for Ketoprofen sodium) and its possible salts and derivatives; compound G or individual compounds thereof, for the (manufacture of a medicament for the) treatment of CMT or a related disorder.

Another object of the invention relates to the use of a compound selected from Acetazolamide (CAS 59-66-5 and CAS 1424-27-7 for sodium form) and its possible salts and derivatives; Aminoglutethimide (CAS 125-84-8) and its possible salts and derivatives; Aztreonam (CAS 78110-38-0 and CAS 80581-86-8 exists for Aztreonam disodium) and its possible salts and derivatives; Baclofen (CAS 1134-47-0 and CAS 63701-56-4 for baclofen-hydrochloride) and its possible salts, prodrugs and derivatives; Balsalazide (CAS 80573-04-2, 150399-21-6 (disodium form), 213594-60-6 (disodium form), and 82101-18-6) and its possible salts and derivatives; Bicalutamide (CAS 90357-06-5) and its possible salts and derivatives; Bromocriptine (CAS 25614-03-3 and CAS 22260-51-1 for mesylate form) and its possible salts and derivatives; Bumetanide (CAS 28395-03-1) and its possible salts and derivatives; Buspirone (CAS 36505-84-7 and CAS 33386-08-2 for hydrochloride form) and its possible salts and derivatives; Ciprofloxacin (CAS 85721-33-1 and CAS 86393-32-0 for hydrochloride form) and its possible salts and derivatives; Clonidine (CAS 4205-90-7 and CAS 4205-91-8 for hydrochloride form) and its possible salts and derivatives; Cyclosporine A (CAS 59865-13-3) and its possible salts and derivatives; Disulfiram (CAS 97-77-8) and its possible salts, prodrugs and derivatives; Exemestane (CAS 107868-30-4) and its possible salts and derivatives; Felbamate (CAS 25451-15-4) and its possible salts and derivatives; Fenofibrate (CAS 49562-28-9) and its possible salts and derivatives; Finasteride (CAS 98319-26-7) and its possible salts and derivatives; Flumazenil (CAS 78755-81-4) and its possible salts and derivatives; Flunitrazepam (CAS 1622-62-4) and its possible salts and derivatives; Furosemide (CAS 54-31-9) and its possible salts and derivatives; Gabapentin (CAS 60142-96-3) and its possible salts and derivatives; Galantamine (CAS 357-70-0 and CAS 1953-04-4 for hydrobromide form) and its possible salts and derivatives; Haloperidol (CAS 52-86-8) and its possible salts and derivatives; Ibuprofen (CAS 15687-27-1 and CAS 31121-93-4 for sodium salt) and its possible salts and derivatives; Isoproterenol (CAS 7683-59-2, CAS 51-30-9 for hydrochloride form, CAS 5984-95-2 (Isoproterenol (−)-hydrochloride)) and its possible salts and derivatives; L-carnitine (CAS 541-15-1 and CAS 6645-46-1 for hydrochloride form) and its possible salts and derivatives; Liothyronine (T3) (CAS 6893-02-3 and CAS 55-06-1 for sodium form) and its possible salts and derivatives; Losartan (CAS 114798-26-4 and CAS 124750-99-8 for potassium form) and its possible salts and derivatives; Loxapine (CAS 1977-10-2, and CAS 27833-64-3 and CAS 54810-23-0 for succinate and hydrochloride forms, respectively) and its possible salts and derivatives; Metaproterenol (CAS 586-06-1 and CAS 5874-97-5 for sulfate form) and its possible salts and derivatives; Metaraminol (CAS 54-49-9 and CAS 33402-03-8 for bitartrate form) and its possible salts and derivatives; Metformin (CAS 657-24-9 and CAS 1115-70-4 for hydrochloride form) and its possible salts and derivatives; Methimazole (CAS 60-56-0) and its possible salts and derivatives; Methylergonovine (CAS 113-42-8 and CAS 57432-61-8 corresponding to maleate salt) and its possible salts and derivatives; Metopirone (CAS 54-36-4) and its possible salts and derivatives; Metoprolol (CAS 37350-58-6, CAS 51384-51-1 and CAS 56392-17-7 (tartate forms)) and its possible salts and derivatives; Mifepristone (CAS 84371-65-3) and its possible salts, prodrugs and derivatives; Nadolol (CAS 42200-33-9) and its possible salts and derivatives; Naloxone (CAS 465-65-6 and CAS 51481-60-8 for hydrochloride dihydrate) and its possible salts and derivatives; Naltrexone (CAS 16590-41-3 and CAS 16676-29-2 for naltrexone hydrochloride) and its possible salts, prodrugs and derivatives; Norfloxacin (CAS 70458-96-7) and its possible salts and derivatives; Pentazocine (CAS 359-83-1, CAS 7361-76-4 for the Pentazocine (+) form, CAS 17146-95-1 for lactate form, CAS 64024-15-3 for hydrochloride form) and its possible salts and derivatives; Phenoxybenzamine (CAS 59-96-1, CAS 63-92-3 for hydrochloride form) and its possible salts and derivatives; Phenylbutyrate (CAS 1716-12-7, which corresponds to sodium form; CAS 1821-12-1 which corresponds to 4-Phenylbutyric acid) and its possible salts and derivatives; Pilocarpine (CAS 92-13-7 and CAS 54-71-7 for pilocarpine hydrochloride) and its possible salts, prodrugs and derivatives; Pioglitazone (CAS 111025-46-8, CAS 112529-15-4 for hydrochloride form) and its possible salts and derivatives; Prazosin (CAS 19216-56-9, CAS 19237-84-4 for hydrochloride form) and its possible salts and derivatives; Raloxifene (CAS 84449-90-1, CAS 82640-04-8 for hydrochloride form) and its possible salts and derivatives; Rifampin (CAS 13292-46-1) and its possible salts and derivatives; Simvastatin (CAS 79902-63-9) and its possible salts and derivatives; D-Sorbitol (CAS 50-70-4) and its possible salts, prodrugs and derivatives; compound Spironolactone (CAS 52-01-7) and its possible salts and derivatives; Tamoxifen (CAS 10540-29-1, CAS 54965-24-1 for citrate form) and its possible salts and derivatives; Trilostane (CAS 13647-35-3) and its possible salts and derivatives; Valproic acid (CAS 99-66-1, CAS 1069-66-5 and CAS 76584-70-8 for sodium and Divalproex sodium forms respectively) and its possible salts and derivatives; Carbamazepine (CAS 298-46-4, CAS 85756-57-6 for dihydrate form) and its possible salts and derivatives; Ketoprofen (CAS 22071-15-4 and CAS 57495-14-4 for Ketoprofen sodium) and its possible salts and derivatives; Flurbiprofen (CAS 5104-49-4, CAS 51543-39-6 and CAS 51543-40-9 corresponding to S and R enantiomers; CAS 56767-76-1 correspondsing to sodium form) and its possible salts and derivatives; Diclofenac (CAS 15307-86-5, CAS 15307-79-6 for sodium form; CAS 15307-81-0 for potassium form) and its possible salts and derivatives; Meloxicam (CAS 71125-38-7) and its possible salts and derivatives; Tacrolimus (CAS 104987-11-3, CAS 109581-93-3 for monohydrate solid form) and its possible salts and derivatives; Diazepam (CAS 439-14-5) and its possible salts and derivatives; Dutasteride (CAS 164656-23-9) and its possible salts and derivatives; Indomethacin (CAS 53-86-1, CAS 74252-25-8 and 7681-54-1 for 2 sodium forms) and its possible salts and derivatives; Dinoprostone (CAS 363-24-6) and its possible salts and derivatives; Carbachol (CAS 51-83-2, CAS 462-58-8 which corresponds to Choline carbonate (ester)) and its possible salts and derivatives; Estradiol (CAS 50-28-2 and 57-91-0 for beta and alpha forms respectively) and its possible salts and derivatives; Curcumin (CAS 458-37-7) and its possible salts and derivatives; Lithium (CAS 7439-93-2, CAS 554-13-2 and 919-16-4 for carbonate and citrate anhydrous forms; CAS 7447-41-8 for chloride form) and its possible salts and derivatives; Rapamycin (CAS 53123-88-9) and its possible salts and derivatives; Betaine (CAS 2218-68-0, for chloral betaine; CAS 107-43-7, 17146-86-0, 590-46-5, 590-47-6 correspond to betaine, Betaine monohydrate, Betaine hydrochloride and Betaine monohydrate forms) and its possible salts and derivatives; Trehalose (CAS 4484-88-2) and its possible salts and derivatives; Amiloride (CAS 2016-88-8, corresponding to hydrochloride anhydrous; CAS 2609-46-3 corresponding to amiloride (identified in IPA)) and its possible salts and derivatives; Albuterol (CAS 18559-94-9, CAS 51022-70-9 for sulfate form) and its possible salts and derivatives, or combination(s) thereof, for the (manufacture of a medicament for the) treatment of CMT or a related disorder.

A further object of this invention relates to the use of a combination of at least two compounds selected from D-Sorbitol (compound A); Baclofen (compound B); Pilocarpine (compound C); Naltrexone (compound D); Methimazole (compound E); Mifepristone (compound F), and Ketoprofen (compound G), or salts or prodrugs thereof, for the (manufacture of a medicament for the) treatment of CMT or a related disorder.

A further object of this invention relates to the use of a compound selected from D-Sorbitol (compound A); Baclofen (compound B); Pilocarpine (compound C); Naltrexone (compound D); Methimazole (compound E); Mifepristone (compound F), and Ketoprofen (compound G), or salts or prodrugs thereof, for the (manufacture of a medicament for the) treatment of CMT or a related disorder.

A further object of this invention relates to the use of a combination of at least two compounds selected from Acetazolamide; Aminoglutethimide; Aztreonam; Baclofen Balsalazide; Bicalutamide; Bromocriptine; Bumetanide; Buspirone; Ciprofloxacin; Clonidine; Cyclosporine A; Disulfiram; Exemestane; Felbamate; Fenofibrate; Finasteride; Flumazenil; Flunitrazepam; Furosemide; Gabapentin; Galantamine; Haloperidol; Ibuprofen; Isoproterenol; L-carnitine; Liothyronine (T3); Losartan; Loxapine; Metaproterenol; Metaraminol; Metformin; Methimazole; Methylergonovine; Metopirone; Metoprolol; Mifepristone; Montelukast; Nadolol; Naltrexone; Naloxone; Norfloxacin; Pentazocine; Phenoxybenzamine; Phenylbutyrate; Pilocarpine; Pioglitazone; Prazosin; Raloxifene; Rifampin; Simvastatin; Spironolactone; Tamoxifen; Trilostane; Valproic acid; Carbamazepine; Ketoprofen; Flurbiprofen; Diclofenac; Meloxicam; D-Sorbitol; Tacrolimus; Diazepam; Dutasteride; Indomethacin; Dinoprostone; Carbachol; Estradiol; Curcumin; Lithium; Rapamycin; Betaine; Trehalose; Amiloride; Albuterol, or salts or prodrugs thereof, for the (manufacture of a medicament for the) treatment of CMT or a related disorder.

Another object of the invention relates to the use of a combination of at least two compounds selected from D-Sorbitol (compound A); Baclofen (compound B); Pilocarpine (compound C); Naltrexone (compound D); Methimazome (compound E); Mifepristone (compound F), Ketoprofen (compound G) or salts or prodrugs thereof, for (the manufacture of a medicament for) reducing PMP22 expression in a subject having CMT or a related disorder.

Another object of the invention relates to the use of a combination of at least two compounds selected from Acetazolamide; Aminoglutethimide; Aztreonam; Baclofen Balsalazide; Bicalutamide; Bromocriptine; Bumetanide; Buspirone; Ciprofloxacin; Clonidine; Cyclosporine A; Disulfiram; Exemestane; Felbamate; Fenofibrate; Finasteride; Flumazenil; Flunitrazepam; Furosemide; Gabapentin; Galantamine; Haloperidol; Ibuprofen; Isoproterenol; L-carnitine; Liothyronine (T3); Losartan; Loxapine; Metaproterenol; Metaraminol; Metformin; Methimazole; Methylergonovine; Metopirone; Metoprolol; Mifepristone; Montelukast; Nadolol; Naltrexone; Naloxone; Norfloxacin; Pentazocine; Phenoxybenzamine; Phenylbutyrate; Pilocarpine; Pioglitazone; Prazosin; Raloxifene; Rifampin; Simvastatin; Spironolactone; Tamoxifen; Trilostane; Valproic acid; Carbamazepine; Ketoprofen; Flurbiprofen; Diclofenac; Meloxicam; D-Sorbitol; Tacrolimus; Diazepam; Dutasteride; Indomethacin; Dinoprostone; Carbachol; Estradiol; Curcumin; Lithium; Rapamycin; Betaine; Trehalose; Amiloride; Albuterol, or salts or prodrugs thereof, for (the manufacture of a medicament for) reducing PMP22 expression in a subject having CMT or a related disorder.

A further object of this invention is a pharmaceutical composition comprising a combination of at least two compounds selected from the group of D-Sorbitol, Baclofen, Pilocarpine, Naltrexone, Methimazole, Mifepristone and Ketoprofen, salts or prodrugs thereof, and a pharmaceutically suitable excipient.

In a preferred embodiment, the above drugs are used in combination(s), to provide the most effective effect. In this respect, a further object of this invention resides in the use of a combination of drugs for treating CMT or a related disorder, wherein said combination is selected from:

an antagonist of a steroid hormone receptor and a compound selected from a muscarinic receptor agonist, a GABA-B receptor agonist, an ERK activator, a pAkt kinase inhibitor, a drug affecting thyroid hormone signalling; a drug affecting the D-sorbitol signalling pathways, an opioid receptor antagonist, COX inhibitor;

a muscarinic receptor agonist and a compound selected from GABA-B receptor agonist, an ERK activator, a pAkt kinase inhibitor, a drug affecting thyroid hormone signalling; a drug affecting the sorbitol signalling pathways, an opioid receptor antagonist; Cox inhibitor;

a GABA-B receptor agonist and a compound selected from an ERK activator, a pAkt kinase inhibitor, a drug affecting thyroid hormone signalling; a drug affecting the sorbitol signalling pathways, an opioid receptor antagonist and Cox inhibitor;

an ERK activator and a compound selected from a pAkt kinase inhibitor, a drug affecting thyroid hormone signalling; a drug affecting the sorbitol signalling pathways, an opioid receptor antagonist Cox inhibitor;

a pAkt kinase inhibitor and a drug affecting thyroid hormone signalling; a compound selected from a drug affecting the sorbitol signalling pathways, an opioid receptor antagonist and Cox inhibitor;

a drug affecting thyroid hormone signalling; and a drug affecting the sorbitol signalling pathways and an opioid receptor antagonist or Cox inhibitor;

a drug affecting the sorbitol signalling pathways and an opioid receptor antagonist or Cox inhibitor an opioid receptor antagonist and Cox inhibitor In a particular aspect, the invention concerns the use of the above compounds or compositions or combinations for the treatment of CMT.

The invention further provides a method for treating CMT or a related disorder, particularly CMT, comprising administering to a subject in need thereof an effective amount of any compound or combination of compounds or composition as disclosed above. A preferred method comprises the administration of a combination of at least two compounds selected from compound A, compound B, compound C, compound D, compound E, compound F, and compound G, or salts or prodrugs thereof.

In this respect, a specific object of this invention is a method of treating CMT1a in a subject, comprising administering to the subject an effective amount of a compound or combination of compounds as disclosed above.

Any of the various uses or methods of treatment disclosed herein can also include an optional step of diagnosing a patient as having CMT or a related disorder, particularly CMT1A, or identifying an individual as at risk of developing CMT or a related disorder, particularly CMT1A.

In this regard, a further object of this invention is a method of treating CMT, particularly CMT1a, the method comprising (1) assessing whether a subject has CMT, particularly CMT1a and (2) treating the subject having CMT, particularly CMT1a with an effective amount of a combination of compounds as described above. Determining whether a subject has CMT, particularly CMT1a, can be done by various tests known per se in the art, such as DNA assays.

The invention may be used for treating CMT or a related disorder in any mammalian subject, particularly human subjects, more preferably CMT1a.

BRIEF DESCRIPTION OF THE DRAWINGS

The invention description below refers to the accompanying drawings.

DETAILED DESCRIPTION

Figure 1:
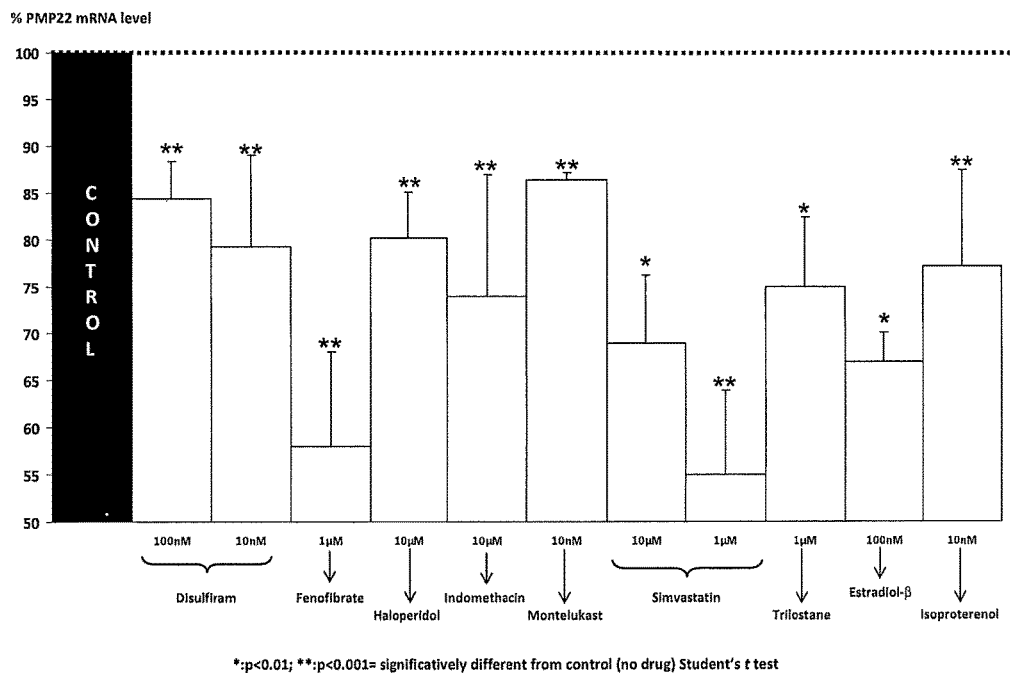
FIG. 1. Effect of selected drugs on PMP22 mRNA expression level.

The present invention provides new therapeutic approaches for treating CMT or related disorders. The invention discloses novel use of drugs or drug combinations which allow an effective correction of such diseases and may be used in any mammalian subject.

Within the context of the present invention, the term "CMT related disorder" designates other diseases associated with abnormal expression, of myelin proteins which include PMP22. The variety of these diseases is due to the variety of PMP22 roles.

PMP22 is firstly a major component of myelin expressed in the compact portion of essentially all myelinated fibers in the peripheral nervous system. PMP22 protein interacts with another structural myelin protein P0, and therefore, the altered PMP22/P0 protein ratio might influence the compaction of myelin sheaths (Vallat et al., 1996; D'Urso et al., 1999). As demonstrated by in vitro studies, PMP22 protein is also involved in the regulation of cell spreading in a Rho-dependent manner and thus could affect axonal ensheathment (Brancolini et al., 1999). Moreover, PMP22 forms complexes with α6β4 integrins and could mediate the interaction of Schwann cells with extracellular matrix (Amici et al., 2006; Amici et al., 2007). Furthermore, increased level of PMP22 protein can alter the Arf6-regulated plasma membrane endosomal recycling pathway and lead to accumulation of PMP22 in the late endosomes (Chies et al., 2003). It was also demonstrated that over expressed PMP22 protein perturbs intracellular protein sorting and overloads the protein degradation machinery in Schwann cells (Notterpek et al., 1997; Tobler et al., 2002; Fortun et al., 2003; Fortun et al., 2006; Fortun et al., 2007; Khajavi et al., 2007). Finally, PMP22 is directly involved in the control of cell proliferation and programmed cell death (Sancho et al., 2001; Atanasoski et al., 2002) and mutant PMP22 protein was shown to provoke profound reorganization and the aberrant expression of axonal ion channels (Ulzheimer et al., 2004; Devaux & Scherer, 2005). PMP22 is also expressed in some parts of human brain (Ohsawa Y et al, 2006). There is evidence for its implication in mood disorders (Le-Niculescu H et al, 2008) and in schizophrenia (Dracheva S et al, 2006). PMP22 is playing a role in establishing brain/blood barrier (Roux K J et al, 2004) that is often defective in multiple sclerosis and neurodegenerative diseases.

Consequently, the term "CMT related disorder" designates Alzheimer's disease (AD), senile dementia of AD type (SDAT), Parkinson's disease, Lewis body dementia, vascular dementia, autism, mild cognitive impairment (MCI), age-associated memory impairment (AAMI) and problem associated with ageing, post-encephalitic Parkinsonism, schizophrenia, depression, bipolar disease and other mood disorders, Huntington's disease, motor neurone diseases including amyotrophic lateral sclerosis (ALS), multiple sclerosis, idiopathic neuropathies, diabetic neuropathy, toxic neuropathy including neuropathy induced by drug treatments, neuropathies provoked by HIV, radiation, heavy metals and vitamin deficiency states, prion-based neurodegeneration, including Creutzfeld-Jakob disease (CJD), bovine spongiform encephalopathy (BSE), GSS, FFI, Kuru and Alper's syndrome.

In a preferred embodiment, CMT related disorder designates a neuropathy, such as demyelinating neuropathies, including HNPP (hereditary neuropathy with liability to pressure palsies), CMT1B, CMT1C, CMT1D, CMT1X, CMT2A, CMT2B, CMT2D, CMT2E, CMT2-P0, severe demyelinating neuropathies DSS (Dejerine-Sottas syndrome), CHN (congenital hypomyelinating neuropathy), CMT4A, CMT4B1, CMT4B2, CMT4D, CMT4F, CMT4, AR-CMT2A, HSN1.

As used herein, "treatment" of a disorder includes the therapy, prevention, prophylaxis, retardation or reduction of pain provoked by the disorder. The term treatment includes in particular the control of disease progression and associated symptoms.

Also, the term compound designates the chemical compounds as specifically named in the application, as well as any pharmaceutically composition with acceptable salt, hydrate, ester, ether, isomers, racemate, conjugates, prodrugs thereof.

Also, the term "combination" designates a treatment wherein at least two drugs are co-administered to a subject to cause a biological effect. In a combined therapy, the at least two drugs may be administered together or separately, at the same time or sequentially. Also, the at least two drugs may be administered through different routes and protocols.

The invention shows that functionality of peripheral myelin protein(s) can be modulated by drugs affecting muscarinic receptor, GABA-B receptor, steroid hormone receptor, opioid receptor, sorbitol signalling pathways, or activating ERK (extracellular signal-regulated kinase), COX inhibitors, thyroid hormone signalling inhibitors and/or inhibiting pAkt kinase, thereby allowing the design of new therapeutic approaches of CMT and related disorders.

Furthermore, the invention discloses the identification and activities of particular drugs which, either in combination(s) or alone modulate the above pathways and may be used to treat said diseases.

More specifically, the invention shows that compound A, compound B, compound C, compound D, compound E, compound F and compound G, either in combination(s) or alone, preferably in combination, can be used to treat CMT or related disorders.

D-Sorbitol (Compound A)

This drug, $C_6H_{14}O_6$, is a member of bladder irrigant, laxative, and hyperosmotic classes.

It has been approved for the treatment of i) Irrigation of Urinary Bladder (Adult) for preventing infection during prostate surgery or other urinary tract surgeries ii) Poisoning (Adult) when mixed with activated charcoal and iii) Constipation (Adult) acting as a hyperosmotic laxative: It works by retaining fluid in the colon, which helps to increase muscle movement in the intestines.

Targeted Metabolic Pathway in the CMT1A Disease:

Extracellular Signal-Regulated Kinase (ERK) and Akt pathways control expression of the PMP22 gene in the opposing manner: transcription of the PMP22 gene is enhanced by the activated PI3K/pAkt/GSK-3β signalling pathway and is suppressed by the Ras/MEK/ERK kinase cascade. Compound A is able to activate ERK/JNK/p38 kinases and, probably, decreases expression of the PMP22 gene by modulating ERK kinase activity ((Bogoyevitch et al., 1995; Galvez et al., 2003).

Misfolded PMP22 protein aggregations provoked by overexpression of PMP22 gene are the integral phenotypic characteristic of CMT1A Schwann cells and might affect intracellular membrane dynamics, protein sorting and degradation. Thus, D-sorbitol, as a cellular osmolyte which possesses a chaperone activity, could additionally suppress deleterious effect of overexpressed PMP22 gene by augmenting capacity of intracellular machinery, implicated in protein folding and clearance (Fortun et al., 2005; Fortun et al., 2006; Welch & Brown, 1996).

Compound A might also exert an enhanced effect via stimulation of muscarinic type 2 receptor to which compound A binds specifically. This leads to a decrease in PMP22 expression.

Finally, compound A suppresses apoptosis and oxidative stress by feedback inhibition of aldose reductase pathway. D-Sorbitol is produced in aldose reductase metabolic pathway. Attenuation of aldose reductase gene suppresses apoptosis and oxidative stress in rat cells (Nambu H et al, 2008)

Baclofen (Compound B)

This drug, $C_{10}H_{12}ClNO_2$, has been approved for the alleviation of signs and symptoms of reversible spasticity resulting from multiple sclerosis, particularly for the relief of flexor spasms and concomitant pain, clonus, and muscular rigidity, and for intrathecal treatment of severe spasticity of spinal cord origin in patients who are unresponsive to or cannot tolerate oral therapy.

Compound B is a direct agonist at GABA-B receptors. Its precise mechanism of action is not fully known. It is capable of inhibiting both monosynaptic and polysynaptic reflexes at the spinal level, possibly by hyperpolarization of afferent terminals, although actions at supraspinal sites may also occur and contribute to its clinical effect.

Targeted Metabolic Pathway in the CMT1A Disease:

GABA(B) receptor was shown to activate ERK1/2 kinases via GPCR interacting scaffolding protein (GISP) and thus could negatively regulate PI3K-Akt-GSK-3β signalling pathway and activity of steroid hormone receptors implicated in positive transcriptional regulation of PMP22 gene in Schwann cells (Kantamneni et al., 2007; Lange et al., 2007; Miller et al., 2007; Tu et al., 2007). Additionally, GABAB receptors can—in a developmental context-dependent manner—decreases activity of GABAA receptors that are also recognized as positive modulators of PMP22 expression (Obrietan & van den Pol, 1998).

Pilocarpine (Compound C)

This drug, $C_{11}H_{16}N_2O_2$, has been approved for the treatment of i) symptoms of dry mouth from salivary gland hypofunction caused by radiotherapy for cancer of the head and neck; and ii) the treatment of symptoms of dry mouth in patients with Sjogren's syndrome.

Agonist of muscarinic receptors, it causes smooth muscle fibers contraction (digestive tract, eye, bronchus), stimulates sudoral, salivary, bronchus and gastric secretions. Furthermore, it exhibits a complex cardiovascular action, stimulating both parasympathomimetic (vasodilation) excitoganglionary pathways.

Targeted Metabolic Pathway in the CMT1A Disease:

We demonstrated that pilocarpine, an agonist of muscarinic receptors, decreases expression of the PMP22 protein in Schwann cells in vitro. Muscarinic receptors are able to modulate both Akt and Erk pathways in different cellular settings and thus, could participate in fine switch control of these two signalling pathways, implicated in positive and negative transcriptional regulation of PMP22 protein respectively. We propose that stimulation of muscarinic receptors by pilocarpine leads, —likely, through complex set of molecular mechanisms, —to shifting in intracellular balance of Erk/Akt activities to more pronounced Erk signalling, inhibiting expression of PMP22 gene. For instance, muscarinic receptors can selectively block signalling by IGF-1 mediated by pAkt/GSK-3β functional module by promoting IRS-1 tyrosine dephosphorylation, which uncouple IRS-1 from the stimulated IGF-1 receptor (Batty et al., 2004; Stirnweiss et al., 2006).

Naltrexone (Compound D)

This drug, $C_{20}H_{23}NO_4$, has been approved for the treatment of alcohol dependence and for the blockade of the effects of exogenously administered opioids.

This drug binds to the opioid mu receptor antagonistically, thereby preventing conventional opiate (heroin, morphine) drugs from binding and inducing opioid neural responses. It markedly attenuates or completely blocks, reversibly, the subjective effects of intravenously administered opioids. When co-administered with morphine, on a chronic basis, it blocks the physical dependence to morphine, heroin and other opioids. In subjects physically dependent on opioids, it will precipitate withdrawal symptomatology.

The mechanism of action in alcoholism is not understood; however, involvement of the endogenous opioid system is suggested by preclinical data. It competitively binds to such receptors and may block the effects of endogenous opioids.

Targeted Metabolic Pathway in the CMT1A Disease:

Extracellular Signal-Regulated Kinase (ERK) and Akt pathways control expression of the PMP22 gene in the opposing manner: transcription of the PMP22 gene is elevated by the activated PI3K/pAkt/GSK-3β signaling pathway and is suppressed by the Ras/MEK/ERK kinase cascade. Compound C, via negative regulation of the σ opioid receptor, could block activity of the pAkt kinase and therefore decreases transcription of the PMP22 gene.

Schwann cells express, though at low levels, all types of opioid and sigma receptors and their natural ligands prodynorphin and proenkephalin, —an observation indicating that an autocrine opioid signalling could play an important role in biology of these glial cells.

Signalling through opioid receptors is extremely complex and varies between acute and chronic agonist application modes. We suggest that naltrexone might attenuate activation of pAkt kinase and down-regulation of Erk kinase-mediated signalling, provoked, —as it was demonstrated for some neuronal cells, —by acute morphine application (Muller and Unterwald, 2004).

Extracellular Signal-Regulated Kinase (ERK) and Akt pathways control expression of the PMP22 gene in the opposing manner: transcription of the PMP22 gene is elevated by the activated PI3K/pAkt/GSK-3β signalling pathway and is suppressed by the Ras/MEK/ERK kinase cascade. Compound C, via negative regulation of the σ opioid receptor, could block activity of the pAkt kinase and augment signalling via Erk kinase, therefore decreasing transcription of the PMP22 gene.

Methimazole (Compound E)

This drug has been approved for the treatment of hyperthyroidism, goiter, Graves disease, and psoriasis.

Methimazole binds and blocks activity of thyroid peroxidase, a rate limiting enzyme in synthesis of thyroid hormones that convert iodide to iodine. Thus, methimazole effectively inhibits the production of new thyroid hormones.

Targeted Metabolic Pathway in the CMT1A Disease:

Though Schwann cells do not express thyroid hormone receptors in intact adult sciatic nerve, disruption of normal axonal-glia interaction in damaged peripheral nerves rapidly induces expression of these receptors in Schwann cells, indicating the importance of thyroid hormone signalling for inducible repair of PNS damage (Walter, 1993). This proposal is additionally supported by the observation that injured sciatic nerves express not only thyroid receptors, but also enzymes involved in metabolism of thyroid hormones—the type 2 deiodinase, converting thyroxine (T4) into triiodothyronine (T3), and the type 3 deiodinase responsible for the degradation of thyroid hormones (Walter et al., 1995; Li et al., 2001). Since overexpression of PMP22 gene in Schwann cells disrupt normal axonal-glia interaction in damaged peripheral nerves of CMT patients, thyroid receptor signalling might also play an important role in progression of Charcot-Marie-Tooth disease.

Triiodothyronine T3 is a strong activator of EGR2 expression in Schwann cells; since the EGR2 transcription factor is recognized as a major positive regulator of promyelinating transcription program in Schwann cells, signalling via thyroid hormone receptors could influence transcription of the PMP22 gene (Mercier et al., 2001). We supposed that methimazole could decrease transcription of PMP22 gene by attenuating thyroid hormone signalling in damaged Schwann cells.

Mifepristone (Compound F)

This drug, $C_{29}H_{35}NO_2$, has been approved for the medical termination of intrauterine pregnancy through 49 days' pregnancy.

The anti-progestational activity of compound F results from competitive interaction with progesterone at progesterone-receptor sites. Based on studies with various oral doses in several animal species (mouse, rat, rabbit and monkey), the compound inhibits the activity of endogenous or exogenous progesterone.

Targeted Metabolic Pathway in the CMT1A Disease:

Compound F is an antagonist of progesterone and glucocorticoid receptors, which are positive regulators of PMP22 transcription.

Though compound F was developed as a progesterone receptor antagonist, it is also recognized as glucocorticoid hormone receptors antagonist; additionally, it displays also a weak anti-androgen activity and does not bind to the estrogen receptor or to the mineralocorticoid receptors.

Transcription of PMP22 protein is positively regulated by several nuclear receptors, including steroid hormone receptors, expressed in Schwann cells (Robert et al., 2001; Schumacher et al., 2001).

We suggest that mifepristone, unspecific antagonist decreasing simultaneously activity of both progesterone and glucocorticoid receptors, could be a more potent negative modulator of PMP22 transcription and thus, a more promising candidate for development of CMT1A-relevant drugs than previously tested progesterone receptor-specific antagonist, which demonstrated rather marginal therapeutic effect, especially in long-term treatment paradigm (Sereda et al., 2003; Meyer zu Horste et al., 2007); this conclusion is also supported by recently published data indicating that glucocorticoid receptors are expressed at least 50 times stronger in Schwann cells than progesterone receptors (Groyer et al., 2006).

Ketoprofen (Compound G)

Ketoprofen has been approved for the treatment of rheumatoid arthritis and osteoarthritis. Compound G is a non-steroidal anti-inflammatory drug that blocks activity of both cylooxygenase-1 (COX-1) and cylooxygenase-2 (COX-2) and due to this effect, inhibits prostaglandin and leukotriene synthesis.

Targeted Metabolic Pathway in the CMT1A Disease:

It was previously demonstrated that Schwann cells express several types of functional prostaglandin EP, prostacyclin IP, trombaxone, cysteinyl leukotriene and leukotriene B4 receptors, possess an inducible COX-2 activity and are able to produce prostaglandin E2, thromboxane A2 and leukotriene LTC4 (Constable et al., 1999; Muja et al., 2001; Woodhams et al., 2007).

Prostaglandins—through their cognate GPCR receptors—could augment activity of Akt signalling pathway, which promotes expression of myelin-related proteins including PMP22. For instance, recent findings suggest that the PGE2 prostaglandin is tightly implicated in metabolism of β-catenin, a down-stream effector of pAkt signalling and activator of promyelinating transcriptional program in Schwann cells (Ogata et al., 2004). It was demonstrated that upon the activation of EP receptors by PGE2, the Gαs subunit binds to Axin/GSK-3β complex and decreases GSK-3β-mediated phosphorylation and degradation of β-catenin. Concomitantly, binding of PGE2 to EP receptors provokes the release of Gβγ subunits, which directly stimulate Akt protein through phosphatidylinositol 3-kinases (PI3K) (Castellone et al., 2006).

Thus, cox-inhibitor ketoprofen (Compound G) could decrease transcription of the PMP22 gene by suppressing autocrine signalling through prostaglandin receptors in Schwann cells, which potentiate activity of β-catenin.

In addition, the invention relates to the use of the following compounds, either in combination(s) or alone or to treat CMT or related disorders: Acetazolamide; Aminoglutethimide; Aztreonam; Baclofen Balsalazide; Bicalutamide; Bromocriptine; Bumetanide; Buspirone; Ciprofloxacin; Clonidine; Cyclosporine A; Disulfiram; Exemestane; Felbamate; Fenofibrate; Finasteride; Flumazenil; Flunitrazepam; Furosemide; Gabapentin; Galantamine; Haloperidol; Ibuprofen; Isoproterenol; L-carnitine; Liothyronine (T3); Losartan; Loxapine; Metaproterenol; Metaraminol; Metformin; Methimazole; Methylergonovine; Metopirone; Metoprolol;

Mifepristone; Montelukast; Nadolol; Naltrexone; Naloxone; Norfloxacin; Pentazocine; Phenoxybenzamine; Phenylbutyrate; Pilocarpine; Pioglitazone; Prazosin; Raloxifene; Rifampin; Simvastatin; Spironolactone; Tamoxifen; Trilostane; Valproic acid; Carbamazepine; Ketoprofen; Flurbiprofen; Diclofenac; Meloxicam; D-Sorbitol; Tacrolimus; Diazepam; Dutasteride; Indomethacin; Dinoprostone; Carbachol; Estradiol; Curcumin; Lithium; Rapamycin; Betaine; Trehalose; Amiloride; Albuterol, As discussed above, the invention further shows that particular cell pathways can be modulated to effectively treat CMT or related disorders. More specifically, the invention shows that functionality of PMP22 that includes its expression, folding or transport or of peripheral myelin protein(s) can be modulated by drugs affecting muscarinic receptor, GABA-B receptor, steroid hormone receptor, opioid receptor, sorbitol signalling pathways, thyroid hormone signalling pathway, or activating ERK (extracellular signal-regulated kinase) or inhibiting pAkt kinase and/or COX inhibitors thereby allowing the design of new therapeutic approaches of CMT and related disorders. Such pathways may be modulated either independently, or in combination, to provide the best possible therapeutic effect.

Generally, types of drug combinations, normalizing expression of the PMP22 gene, are being proposed for therapeutic treatment of CMT or related disorders:

(I)—combinations of drugs affecting the same cellular pathway implicating in functioning of the PMP22 gene and its protein, (II)—combinations of drugs modulating different signalling pathways, which converge on in functioning of the PMP22 gene and its protein (III)—combinations of drugs modulating different signalling pathway, which control the functioning of the PMP22 gene and its protein product.

These combinations produce additive or synergistic effects on transcription of the PMP22 gene, and therefore, should allow to significantly decrease effective therapeutic doses of selected drugs and to minimize their undesirable side effects.

Preferred drug combinations according to this invention are selected from:

an antagonist of a steroid hormone receptor and a compound selected from a muscarinic receptor agonist, a GABA-B receptor agonist, an ERK activator, a pAkt kinase inhibitor, a drug inhibiting thyroid hormone signalling a drug affecting the sorbitol signalling pathways, an opioid receptor antagonist, a COX inhibitor;

a muscarinic receptor agonist and a compound selected from GABA-B receptor agonist, an ERK activator, a pAkt kinase inhibitor, a drug inhibiting thyroid hormone signalling a drug affecting the sorbitol signalling pathways, an opioid receptor antagonist; a COX inhibitor;

a GABA-B receptor agonist and a compound selected from an ERK activator, a pAkt kinase inhibitor, a drug inhibiting thyroid hormone signalling a drug affecting the sorbitol signalling pathways, an opioid receptor antagonist and a COX inhibitor;

an ERK activator and a compound selected from a pAkt kinase inhibitor, a drug inhibiting thyroid hormone signalling a drug affecting the sorbitol signalling pathways, an opioid receptor antagonist and a COX;

a pAkt kinase inhibitor and a compound selected from a drug inhibiting thyroid hormone signalling; a drug affecting the sorbitol signalling pathways, an opioid receptor antagonist and a COX inhibitor;

a drug inhibiting thyroid hormone signalling and a compound selected from a drug affecting the sorbitol signalling pathways and an opioid receptor antagonist or a COX inhibitor;

a drug affecting the sorbitol signalling pathways and a compound selected from an opioid receptor antagonist or a COX inhibitor; and an opioid receptor antagonist and a COX inhibitor Preferred examples of drug combinations are selected from:

an antagonist of a steroid hormone receptor and a muscarinic receptor agonist;

an antagonist of a steroid hormone receptor and a GABA-B receptor agonist;

an antagonist of a steroid hormone receptor and an ERK activator;

an antagonist of a steroid hormone receptor and a pAkt kinase inhibitor;

an antagonist of a steroid hormone receptor and thyroid hormone signalling inhibitor;

an antagonist of a steroid hormone receptor and COX inhibitor;

a muscarinic receptor agonist and a GABA-B receptor agonist;

a muscarinic receptor agonist and an ERK activator;

a muscarinic receptor agonist and a pAkt kinase inhibitor;

a muscarinic receptor agonist and thyroid hormone signalling inhibitor;

a muscarinic receptor agonist and COX inhibitor;

a OABA-B receptor agonist and an ERK activator;

a GABA-B receptor agonist and a pAkt kinase inhibitor;

a GABA-B receptor agonist and thyroid hormone signalling inhibitor; and a GABA-B receptor agonist and COX inhibitor or an ERK activator and a pAkt kinase inhibitor;

an ERK activator and thyroid hormone signalling inhibitor;

an ERK activator and COX inhibitor;

or thyroid hormone signalling inhibitor and COX inhibitor

In a particular embodiment, the antagonist of a steroid hormone receptor is compound F, the muscarinic receptor agonist is compound A or compound C, the GABA-B receptor agonist is compound B or compound E, the pAkt kinase inhibitor is compound D, the ERK activator is compound A.

A particular embodiment of the invention resides in a combination therapy for treating CMT or a related disorder, wherein said combination therapy comprises compound A and at least a second compound selected from an antagonist of a steroid hormone receptor, a muscarinic receptor agonist, a GABA-B receptor agonist, an ERK activator, a pAkt kinase inhibitor, an opioid receptor antagonist, COX inhibitor and inhibitor or thyroid hormone signalling.

A particular embodiment of the invention resides in a combination therapy for treating CMT or a related disorder, wherein said combination therapy comprises compound B and at least a second compound selected from an antagonist of a steroid hormone receptor, a muscarinic receptor agonist, an ERK activator, a pAkt kinase inhibitor, a drug affecting the sorbitol signalling pathways, an opioid receptor antagonist COX inhibitor and inhibitor or thyroid hormone signalling.

A particular embodiment of the invention resides in a combination therapy for treating CMT or a related disorder, wherein said combination therapy comprises compound C and at least a second compound selected from an antagonist of a steroid hormone receptor, a GABA-B receptor agonist, an ERK activator, a pAkt kinase inhibitor, a drug affecting the sorbitol signalling pathways, an opioid receptor antagonist COX inhibitor and inhibitor or thyroid hormone signalling.

A particular embodiment of the invention resides in a combination therapy for treating CMT or a related disorder, wherein said combination therapy comprises compound D and at least a second compound selected from an antagonist of a steroid hormone receptor, a muscarinic receptor agonist, a GABA-B receptor agonist, a drug affecting the sorbitol signalling pathways, an ERK activator COX inhibitor and inhibitor or thyroid hormone signalling.

A particular embodiment of the invention resides in a combination therapy for treating CMT or a related disorder, wherein said combination therapy comprises compound E and at least a second compound selected from an antagonist of a steroid hormone receptor, a muscarinic receptor agonist, a drug affecting the sorbitol signalling pathways, an ERK activator, a pAkt kinase inhibitor, an opioid receptor antagonist, COX inhibitor and inhibitor or thyroid hormone signalling.

A particular embodiment of the invention resides in a combination therapy for treating CMT or a related disorder, wherein said combination therapy comprises compound F and at least a second compound selected from a muscarinic receptor agonist, a GABA-B receptor agonist, an ERK activator, a pAkt kinase inhibitor, a drug affecting the sorbitol signalling pathways, an opioid receptor antagonist COX inhibitor and inhibitor or thyroid hormone signalling.

Specific and preferred examples of drug combinations comprise as active substances at least:

(I) compound F and compound E
(II) compound C and compound B
(III) compound F and compound C
compound F and compound B
compound F and compound A
compound F and compound D
compound C and compound A
compound C and compound D
compound B and compound A
compound B and compound D
compound A and compound D
compound G and compound D Therapy according to the invention may be performed as drug combination or alone and/or in conjunction with any other therapy. It and may be provided at home, the doctor's office, a clinic, a hospital's outpatient department, or a hospital, so that the doctor can observe the therapy's effects closely and make any adjustments that are needed.

The duration of the therapy depends on the stage of the disease being treated, the age and condition of the patient, and how the patient responds to the treatment.

Additionally, a person having a greater risk of developing an additional neuropathic disorder (e.g., a person who is genetically predisposed to or have, for example, diabetes, or is being under treatment for an oncological condition, etc.) may receive prophylactic treatment to alleviate or to delay eventual neuropathic response.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers both drugs.

Formulation of Pharmaceutical Compositions

The administration of each drug of the combination may be by any suitable means that results in a concentration of the drug that, combined with the other component, is able to correct the effect of elevated expression of PMP22 upon reaching the peripheral nerves.

While it is possible for the active ingredients of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and is may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

The two drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The emulsifying agents may be naturally occurring gums (e.g., gum acacia or gum tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of two or more drugs that are subjects of this invention can be used together for the preparation of a medicament useful for reducing the effect of increased expression of PMP22 gene, preventing or reducing the risk of developing CMT1A disease, halting or slowing the progression of CMT1A disease once it has become clinically manifest, and preventing or reducing the risk of a first or subsequent occurrence of an neuropathic event.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration will be indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in the combination preferred for a unit dosage will depend upon several factors including the administration method, the body weight and the age of the patient, the severity of the neuropathic damage caused by CMT1A disease or risk of potential side effects considering the general health status of the person to be treated.

Additionally, pharmacogenomic (the effect of genotype on the pharmacokinetic, pharmacodynamic or efficacy profile of a therapeutic) information about a particular patient may affect the dosage used.

Except when responding to especially impairing CMT disease cases when higher dosages may be required, or when treating children when lower dosages should be chosen, the preferred dosage of each drug in the combination will usually lie within the range of doses not above the usually prescribed for long-term maintenance treatment or proven to be safe in the large phase 3 clinical studies.

For example, for compound F from about 2 to about 100 mg per day if taken orally. The special doses should be chosen if administered topically.

for compound D from about 1 to about 20 mg per day if day if taken orally.

for compound B from about 2 to about 20 mg per day if taken orally. The different doses may be suitable if administered in form of nanoparticles or similar formulations.

for compound E from about 125 to about 500 mg per day if taken orally for compound C from about 1 to about 20 mg per if taken orally.

for compound A from about 1 to about 50 g per day if taken orally. The special doses should be chosen if injected.

The most preferred dosage will correspond to amounts from 1% up to 10% of those usually prescribed for long-term maintenance treatment.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

Examples

1. Cell Culture 1.1: Commercially Available Rat Primary Schwann Cells

Vials of rat Schwann cells (SC) primary culture (Science11 #R1700) are defrost and seeded at the density of 10,000 cells/cm$^2$ in "Science11 Schwann cell medium" (basal medium from Science11 #R1701) in poly-L-lysine pre-coated 75 cm$^2$ flasks. The culture medium is composed of basal medium, 5% Fetal Bovine Serum (3H-Biomedical AB #1701-0025), 1% Schwann cell growth supplement (3H Biomedical AB #1701-1752), 1% Gentamicin (Sigma #G1397) and 10 µM of Forskolin (Sigma #F6886) to promote their proliferation.

After reaching confluency (4 to 10 days depending on cell batch), Schwann cells are purified by gentle agitation or by thy1.1 immunopanning that allow SC isolation from adherent fibroblasts, to produce cultures that are at least 95% pure. SC are then counted (Tryptan blue method) and seeded in poly-L-lysine pre-coated 75 cm$^2$ flask in the same SC medium. At confluency, cells are rinsed, trypsinized (trypsin-EDTA 1× diluted from Invitrogen #1540054), diluted in PBS without calcium and magnesium) counted and platted in 12 well-dishes (140,000 cells/well) in Science11 Schwann cell medium with 5% of FBS, 1% of cell growth supplement (CGS), 40 µg/ml of gentamicin and 4 µM Forskolin.

1.2 Custom-Made Rat Primary Schwann Cells

Primary Schwann cell cultures (SC) are established from Sprague-Dawley newborn rats (between P0 and P2) sciatic nerves. All newborn rats are sacrificed and isolated in a Petri dish. Dissection is performed under sterile conditions.

The dorsal skin is removed from the hind paw and the lower torso. The sciatic nerve is isolated and transferred to a culture dish containing ice-cold Leibovitz (L15, Invitrogen #11415) supplemented with 1% penicillin/streptomycin solution (50 UI/ml and 50 µg/ml, respectively; Invitrogen #15070) and 1% of bovine serum albumin (BSA, Sigma A6003). Both nerves per rats are transferred in a 15 ml tube containing ice-cold L15. The L15 medium is then removed and replaced by 2.4 ml of DMEM (Invitrogen #21969035) with 10 mg/ml of collagenase (Sigma #A6003). Nerves are incubated in this medium for 30 minutes at 37° C. The medium is then removed and both nerves are dissociated by trypsin (10% trypsin EDTA 10×, Invitrogen #15400054) diluted in PBS without calcium and magnesium (Invitrogen #2007-03) for 20 min. at 37° C. The reaction is stopped by addition of DMEM containing DNase I grade II (0.1 mg/ml Roche diagnostic #104159) and foetal calf serum (FCS 10%, Invitrogen #10270). The cell suspension was triturated with a 10 ml pipette and passed through a filter in a 50 ml tube (Swinnex 13 mm filter units, Millipore, with 20 µm nylon-mesh filters, Fisher). The cell suspension is centrifuged at 350 g for 10 min at room temperature (RT) and the pellets are suspended in DMEM with 10% FCS and 1% penicillin/streptomycin. Cells are counted (Tryptan blue method) and seeded in Falcon 100 mm Primaria tissue culture plates at the density of $5.10^5$ to $10^6$ cells/dish.

After one day of culture, the medium is changed with DMEM, 10% FCS, 1% penicillin/streptomycin and 10 µM of cytosine b-D-arabinofuranoside (Sigma #C1768). 48 hrs later, medium is eliminated and cells are washed three times with DMEM. The SC growth medium is then added, composed of DMEM, 10% FCS, 1% penicillin/streptomycin, 2 µM of Forskolin (Sigma #F6886), 10 µg/ml of bovine pituitary extract (PEX, Invitrogen #13028). The medium is replaced every 2-3 days.

After 8 days of culture (4 to 10 days depending on cell batches), Schwann cells reach confluency and the culture, containing a large amount of contaminating fibroblasts, is purified by the thy1.1 immunopanning method. After this purification; cells are suspended in growth medium at 10,000 cells/cm$^2$ in poly-L-lysine pre-coated 75 cm$^2$ flasks. Once they reach confluency, cells are rinsed, trypsinized (trypsin-EDTA), counted and platted in 12 well-dishes (100,000 cells/well).

1.3: Drug Incubation

After cells being platted in 12 well-dishes, the medium is replaced by a defined medium consisting in a mix of DMEM-F12 (Invitrogen #21331020) complemented by 1% of N2 supplement (Invitrogen #17502), 1% L-Glutamine (Invitrogen #25030024) 2.5% FBS (Sciencell #0025), 0.02 µg/ml of corticosterone (Sigma #C2505), 4 µM Forskolin and 50 µg/ml of gentamycin. Growth factors are not added to this medium, to promote SC differentiation 24 hours later, the medium is replaced by a defined medium (DMEM-F12) complemented with 1% Insulin-Transferrin-Selenium-X (ITS, Invitrogen #51300), 16 µg/ml of Putrescine (Sigma #P5780), 0.02 µg/ml of corticosterone and 50 µg/ml of gentamicin. At this step, neither progesterone nor forskolin are present in the medium.

One day later, Schwann cells are stimulated by combinations of drugs or drugs alone during 24 hrs (3 wells/condition). The preparation of each compound is performed just prior to its addition to the cell culture medium.

Drugs are added to a defined medium composed of DMEM-F12, with 1% Insulin-Transferrin-Selenium-X (ITS, Invitrogen #51300), 16 µg/ml of Putrescine, 0.02 µg/ml of corticosterone, 10 nM Progesterone and 50 µg/ml of gentamicin. The absence of Forskolin during drug stimulation avoids adenylate cyclase saturation.

2. Schwann Cells Purification by Thy1.1 Immunopanning.

To prevent fibroblast culture contamination, Schwann cells are purified using the clone Thy1.1 (ATCC TIB-103™) immunopanning protocol.

Antibody pre-coated 100 mm bacteria Petri dishes are prepared as follows: these dishes are washed three times with PBS and treated by 20 ml of Tris HCl solution 50 mM, pH 9.5, with 10 µg/ml of goat Anti-Mouse IgM MU antibody (Jackson ImmunoResearch #115-005-020) overnight at 4° C.; then rinsed 3 times with PBS and treated by a solution of PBS with 0.02% of BSA and supernatant obtained from T11D7e2 hybridoma culture (ATCC #TIB-103) containing the Thy1.1 IgM antibody for 2 hours at room temperature. Finally, the plates are washed three times with PBS before the cell suspensions are added.

SC are detached with trypsin EDTA. As soon as the majority of cells are in suspension, the trypsin is neutralized with DMEM-10% FBS and the cells are centrifuged. The pellet of dissociated cells is resuspended in 15 ml of medium with 0.02% BSA at the density of $0.66 \times 10^6$ cells per ml (maximum) and transferred to Petri dish (about 6.6 million of cells/10 ml/dish of 100 mm).

The cell suspension is incubated in the Thy 1.1 coated Petri dish during 45 min at 37° C. with gentle agitation every 15 min to prevent non-specific binding. The majority of fibroblast cells expressing Thy1.1 adhere on the dish. At the end of the incubation, the cell suspension is recovered and centrifuged. This cell suspension contains in theory only Schwann cells. Cells are centrifuged and cell pellet is suspended in growth medium with 10 µM of Forskolin at 16,000 cells/cm$^2$ in T75 cm$^2$ flask Poly-L-Lysine treated.

3-Quantitative Reverse Transcriptase Polymerase Chain Reaction (Q-RT-PCR)

Quantitative RT-PCR is used to compare the levels of PMP22 mRNA after drug stimulation, relative with housekeeping Ribosomal L13A mRNA in rat Schwann cell primary culture.

After rinsing with cold sterilized PBS, total RNAs from each cell sample are extracted and purified from SC using the Qiagen RNeasy micro kit (Qiagen #74004). Nucleic acids are quantified by Nanodrop spectrophotometer using 1 µl of RNA sample. The RNA integrity is determined through a BioAnalyzer (Agilent) apparatus.

RNAs are reverse-transcribed into cDNA according to standard protocol. cDNA templates for PCR amplification are synthesized from 200 ng of total RNA using SuperScript II reverse-transcriptase (Invitrogen #18064-014) for 60 min at 42° C. in the presence of oligo(dT), in a final volume of 20 µl.

cDNAs are subjected to PCR amplification using the «LightCycler® 480» system (Roche Molecular Systems Inc.) Each cDNA are diluted five times before being used for PCR amplification. 2.5 µl of this cDNAs enters the PCR reaction solution (final volume of 10 µl). Preliminary experiments ensured that quantitation was done in the exponential phase of the amplification process for both sequences and that expression of the reference gene was uniform in the different culture conditions.

PCR reaction is performed by amplification of 500 nM of forward primer of rat PMP22 (NM_017037), 5-GGAAACGCGAATGAGGC-3 (SEQ ID NO: 1), and 500 nM of reverse primer 5-GTTCTGTTTGGTTTGGCTT-3 (SEQ ID NO: 2) (amplification of 148-bp). A 152-bp fragment of the RPL13A ribosomal (NM_173340) RNA is amplified in parallel in separate reactions for normalization of the results by using 500 nM of forward primer 5-CTGC-CCTCAAGGTTGTG-3 (SEQ ID NO: 3), and 500 nM of reverse primer 5-CTTCTTCTTCCGGTAATGGAT-3 (SEQ ID NO: 4).

We used FRET chemistry to perform RT-Q-PCR analysis. FRET probes are composed of 0.3 µM of Pmp22-FL-5-GCTCTGAGCGTGCATAGGGTAC (SEQ ID NO: 5) or Rpl13A-FL-5-TCGGGTGGAAGTACCAGCC (SEQ ID NO: 6), labelled at their 3' end with a donor fluorophore dye (Fluorescein). 0.15 µM Red640 probes are defined as follows: Pmp22-red-5'-AGGGAGGGAGGAAGGAAACCA-GAAA (SEQ ID NO: 7) or Rpl13A-red-5'TGACAGC-TACTCTGGAGGAGAAACGGAA (SEQ ID NO: 8), labelled at their 5' end with an acceptor fluorophore dye (Rhodamine Red 640).

Each PCR reaction contained 2.5 µl cDNA template in a final volume of 10 µl of master mix kit (Roche #04-887301001).

The following PCR conditions are used: 10 sec at 95° C., 10 sec at 63° C. and 12 sec at 72° C. and 30 sec at 40° C. (Forty amplification cycles). The relative levels of PMP22 gene expression is measured by determining the ratio between the products generated from the target gene PMP22 and the endogenous internal standard RPL13A.

4-PMP22 Protein Expression Analysis by Flow Cytometry (FACS)

8 hrs, 24 hrs and 48 hrs after drugs incubation, supernatants are recovered, centrifuged and frozen. SC are detached with trypsin-EDTA. As soon as the majority of cells are in suspension, the trypsin is neutralised using DMEM with 10% FCS.

Supernatants with cells are recovered and centrifuged. The pellets of cells are transferred in micro tubes, washed in PBS once and fixed with a specific solution (AbCys #Reagent A BUF09B). 10 minutes later, cells are rinsed once with PBS and kept at 4° C.

Five days after cell fixation, all cell preparations with different incubation times are labelled using the following protocol.

Cells are centrifuged at 7000 rpm for 5 minutes and the pellets are suspended in a solution of permeabilization (AbCys #Reagent B BUF09B) and labelled with primary PMP22 antibody (Abcam #ab61220, ⅕) for 1 hr room at temperature. Cells are then centrifuged at 7000 rpm for 5 minutes and cell pellets are rinsed once in PBS. A secondary antibody is added, coupled to Alexa Fluor 488 (goat anti-rabbit IgG, Molecular Probes #A11008, 1/100), for one hour at room temperature. Cells are then centrifuged at 7000 rpm for 5 minutes and cell pellets are rinsed once in PBS. The labelling is increased adding a tertiary antibody coupled to Alexa Fluor 488 (chicken anti-goat IgG, Molecular Probes #A21467, 1/100) for one hour incubation, at room temperature. Cells are then rinsed once in PBS. Control without any antibody (unlabelled cells) is performed to determine the level of auto-fluorescence and adapted the sensitivity of the photomultipliers. Control with both secondary and tertiary antibodies but without primary antibody, is performed to assess non-specific binding of antibodies.

Data acquisition and analysis are performed with a FACS Array cytometer and FACS Array software (Becton Dickinson) on 5000 cells. Forward Scatter (FSC) correlated with cell volume (size) and Side Scatter (SSC) depending on inner complexity of cells (granularity) are analysed. For expression of PMP22, analysis is performed within the total cells and percent of positive cells is calculated. Positive cells are cells with fluorescence intensity higher than the control with secondary antibody.

In order to quantify the number of SC, cells in control medium are analysed using antibodies anti-S100 Protein.

Cells are prepared according to the following protocol: Schwann cells are stained with antibody anti-S100 Protein (Dako #S0311, 1/100) for 1 hr room at temperature. This antibody is labelled according to protocol described above for PMP22 immunostaining but without incubation with tertiary antibody.

5. Drug Incubation and Activity

Drugs are incubated for 24 hrs or 48 hrs in the same defined medium than described above (3 wells/condition) in absence of Forskolin to avoid adenylate cyclase stimulation saturation, but in presence of 10 nM of progesterone. After drug incubation, supernatants are recovered and Schwann cells are frozen for RT-Q-PCR analysis.

We determined drug activity toward PMP22 expression when it significantly decreases PMP22 levels compared to control. Table 1 below summarizes the results for 20 active drugs that caused PMP22 expression decrease.

TABLE 1

| Compound | mRNA | Protein |
|---|---|---|
| Baclofen | + | |
| Methimazole | + | + |
| Mifepristone | + | |
| Naltrexone | + | |

TABLE 1-continued

| Compound | mRNA | Protein |
|---|---|---|
| Pilocarpine | + | + |
| Sorbitol | + | |
| Disulfiram | + | |
| Fenofibrate | + | |
| Haloperidol | + | |
| Indomethacin | + | |
| Montelukast | + | |
| Simvastatin | + | |
| Trilostane | + | |
| Estradiol-b | + | |
| Isoproterenol | + | |
| Diclofenac | + | + |
| Flurbiprofen | + | + |
| Indomethacin | + | + |
| Ketoprofen | + | + |
| Meloxicam | + | + |

Figure 2:
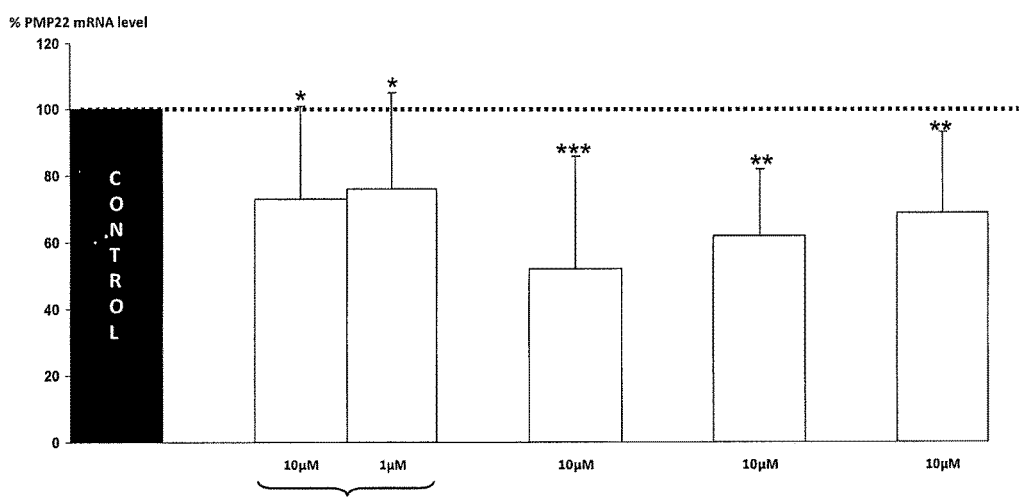
FIG. 2. Effect of selected drugs on PMP22 mRNA expression level.
Figure 3:
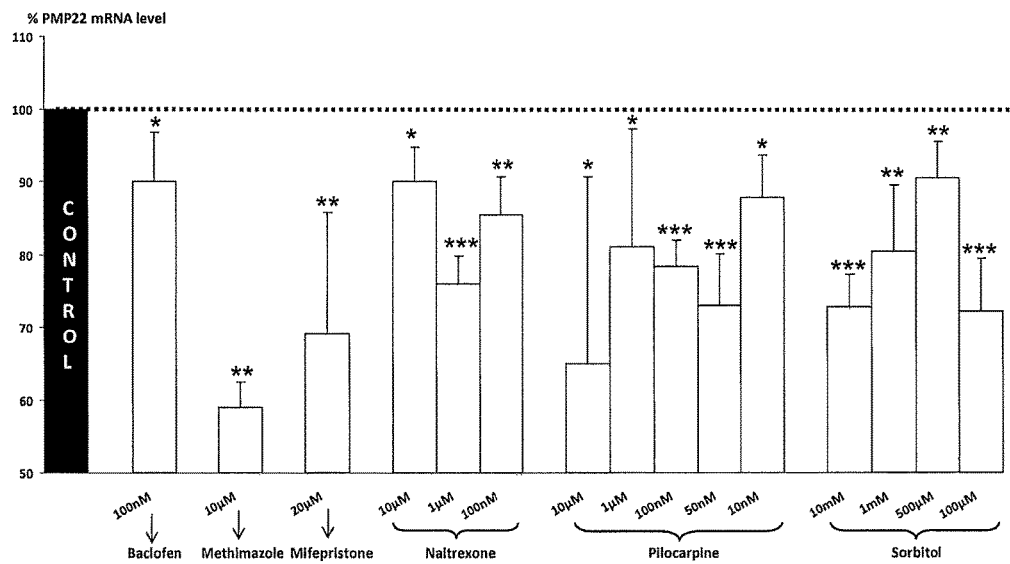
FIG. 3. Effect of selected drugs at various doses on PMP22 mRNA expression level.

The data for 18 drugs that result in a significant decrease of PMP22 mRNA expression after 24 hrs of incubation is illustrated in FIGS. 1-3. These data show substantial reduction in PMP22 mRNA levels, even at very low doses.

Figure 4:
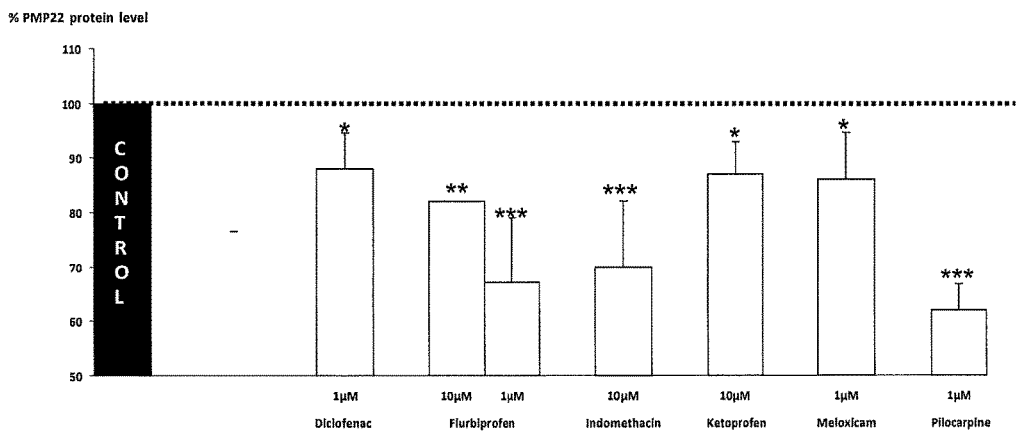
FIG. 4. Effect of selected drugs on PMP22 protein expression level.

6. PMP22 Protein Level After 24 hrs of Incubation:

We tested the ability of some drugs to inhibit PMP22 protein expression (FACS analysis). FIG. 4 describes the results for 6 drugs and show that they are able to decrease significantly PMP22 protein expression, 24 hrs after their addition to the culture medium. The results of the action of some individual drugs on the protein level of PMP22 are also shown on table 1 above.

Figure 5:
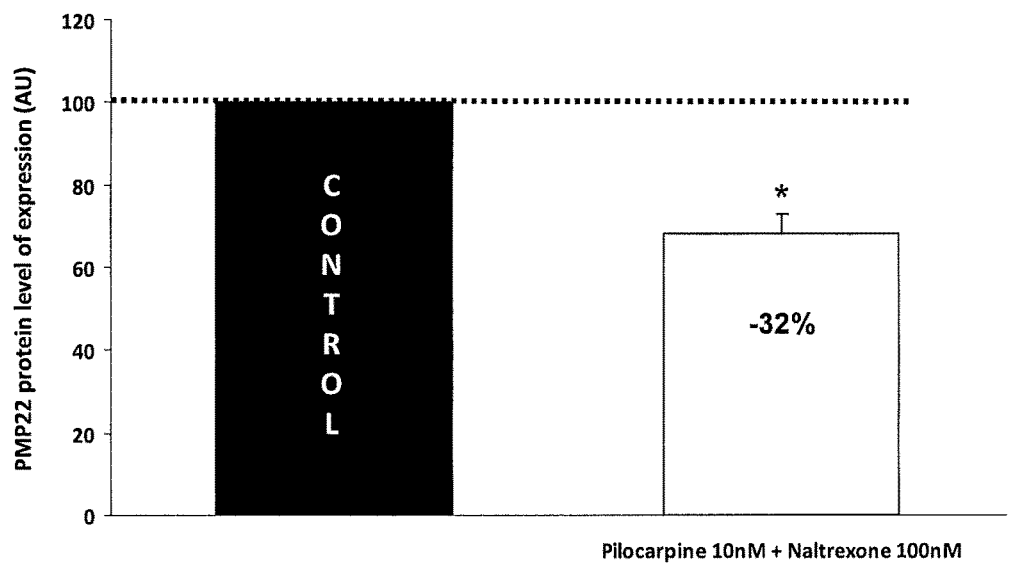
FIG. 5. Effect of combination of Pilocarpine and Naltrexone on PMP22 protein expression level.

In FIG. 5 the effect of a combination of pilocarpine and Naltrexone on PMP22 protein expression after 24 hrs of incubation are shown. The levels of protein expression were compared to untreated controls. These differences were shown to be statistically significant.

Table 2 below summarizes the results obtained with various drug combinations, at various concentrations, on PMP22 protein expression. These results were statistically significant and demonstrate the advantage and beneficial effect of the proposed drug combinations.

TABLE 2

| Combination | % PMP22 FACS | % sd | VARIATION | p value |
|---|---|---|---|---|
| Sorbitol 1 mM + Methimazole 1 µM | 75 | 8 | −25% | p < 0.001 |
| Sorbitol 100 µM + methimazole 10 µM | 74 | 7 | −26% | p < 0.001 |
| Sorbitol 100 µM + methimazole 1 µM | 74 | 7 | −26% | p < 0.001 |
| Pilocarpine 10 nM + Naltrexone 1 µM | 63 | 6 | −37% | p < 0.0001 |
| Pilocarpine 10 nM + Naltrexone 100 nM | 68 | 5 | −32% | p < 0.0001 |
| Sorbitol 1 mM + Naltrexone 1 µM | 67 | 10 | −33% | p < 0.0001 |
| Sorbitol 1 mM + Naltrexone 100 nM | 70 | 10 | −30% | p < 0.0001 |
| Sorbitol 100 µM + Naltrexone 1 µM | 70 | 12 | −30% | p < 0.001 |
| Sorbitol 100 µM + Naltrexone 100 nM | 62 | 14 | −38% | p < 0.0001 |

7. Experiments In Vivo in CMT Animal Model

We tested the compounds for therapeutic effect in a CMT transgenic rat model—a hemizygous PMP22 transgenic rat bearing three additional copies of mouse PMP22 gene (Sereda et al., 1996; Grandis et al., 2004). This CMT rat model is a good approximation of human CMT1A disease from a clinical point of view. Adult CMT rats exhibit a slowing of motor nerve conduction velocity with values similar to those of CMT1A patients, i.e., less than 50%. After sciatic nerve stimulation, compound muscle action potentials show reduced amplitudes and desynchronization. The histological and electrophysiological changes precede the overt clinical signs of motor impairment (Sereda et al., 1996, 2003). Axonal loss, confirmed by histological pronounced muscle atrophy, matches the human CMT1A symptoms.

Four weeks-old rats transgenic PMP22 rats have been used throughout of the study. Aspects of the study design (randomization, statistics for multiple comparisons, sample size etc.) have been checked to be in line with the recommendations provided in $4^{th}$ issue of $43^{rd}$ volume of ILAR Journal (2002), that provides reviews in the field of experimental design and statistics in biomedical research.

The experimental groups are formed with young rats of both genders separately. The rats are assigned to the groups following randomization schedule based on the body weight. In some experiments the randomization is based on the performances of the rats in the bar test.

Both genders are represented by separate control groups that are numerically equal or bigger than the treatment groups.

The rats are treated chronically with drugs—force fed or injected by Alzet osmotic subcutaneous pump (DURECT Corporation Cupertino, Calif.), depending on each drug bioavailability during 10-20 weeks.

The animals are weighted twice a week in order to adjust the doses to growing body weight. If the osmotic pump is chosen for the treatment administration, the doses of the drug are calculated on the basis of the estimated mean body weight of the animals expected for their age over the period of the pump duration (6 weeks). The pumps are re-implanted if necessary, with the appropriated aesthesia protocol.

Behavioral Tests

Each three or four weeks the animals are subjected to a behavioral test. Each test is conducted be the same investigator in the same room and at the same time of the day; this homogeneity is maintained throughout entire experiment. All treatments are blinded for the investigator. "Bar test" and "Grip strength" has been mainly used to access the performance throughout study. The schedule of the bar test may change as the animal growth (in order to avoid the bias due to the learning, for example).

The assay of the grip strength allows detection of subtle differences in the grip performance that seems to be composed of the muscle force, sensitivity status (for instance, painful tactile feelings may change measured values of the force), behavioural component ("motivation"). The values differ between fore and hind limbs and greatly depend on the age of the animals.

The grip strength test measures the strength with which an animal holds on to a grip with its forepaws or its hindpaws separately. A dynamometer is placed with a grip to measure the strength (Force Gauge FG-5000A). The rat is held by the experimenter in a way that it grasps the grip either with its forepaws or with its hind paws and pulls gently the rat backwards until it releases the grip. The force measured when the animal releases the grip is recorded.

Two successive trials measuring the forepaws and two successive trials measuring the hindpaws strength per animal are processed; only the maximum score (one for forepaws and one for hindpaws) is noticed (in N).

The Bar Test evaluates rats' ability to hold on a fix rod. Pmp22 rats which display muscular weakness, exhibit a performance deficit in this test (Sereda et al, 1996). The rat is placed on its four paws on the middle of the rod (diameter: 2.5 cm; length: 50 cm; 30 cm above the table). Trials are performed consecutively; the number and the duration of trials in our experiments have been depending on batches of the animals. This variability in the testing has been introduced in order to determine the schedule appropriated to the best detection of the motor deficiency in the CMT rats in the course of the experiments. Performance indices are recorded on each session:

The number of trials needed to hold for 60 sec (or 30 sec for batch 1, session 1 and 2) on the rod.

The time spent on the bar (i.e. the fall latency) in each trial and the average on the session. In the experimental procedures where the session ends after the rat has stayed for a cut-off time, i.e. 30 or 60 s, on the bar, a performance of the cut-off time (30 s or 60 s) is assigned to trials not completed (eg: for batch 8, for an animal which stays on the bar less than 10 sec on trials 1, 2 and 3, then for 60 sec on trials 4 and 5, 60 s is assigned to trials 6 to 10).

The number of falls.

General Health Assessment

Body weights, overt signs (coat appearance, body posture, gait, tremor etc.) of the animals are monitored throughout the experiment. The rating scale is used for recording: 0=normal, 1=abnormal.

Further Tests

When appropriate, the rats are subjected to electrophysiological evaluation and histological measurement.

Results

Methimazole improved bar test performances throughout the treatment procedure (FIG. 6), while compound PXT25, which is presented here only for the sake of comparison, hardly shows any improvement.

Figure 6:
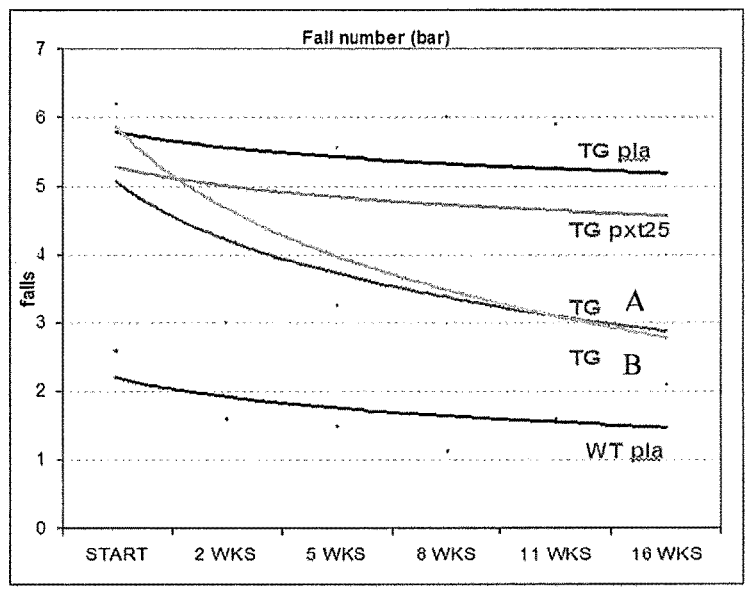
FIG. 6: Results of the motor assessment of the female rats in the Bar-test throughout the treatment study presented in form of trends. A: Methimazole; B: Pilocarpine.

Similarly, Pilocarpine improved bar test performances throughout the treatment procedure (FIG. 6).

Figure 7:
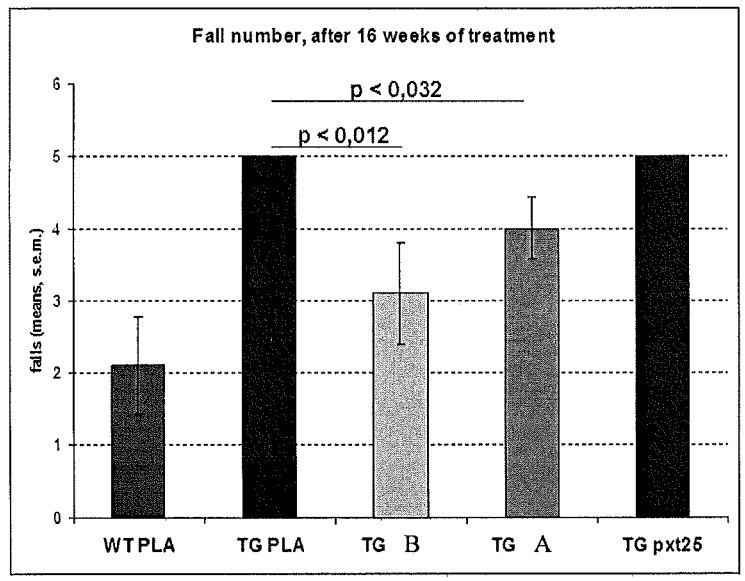
FIG. 7: The mean bar-test performances recorded in this test after 16 weeks of treatment. A: Methimazole; B: Pilocarpine.

The motor performances were on average 3-fold less successful in different CMT rats treated with placebo compared with Wild type (WT) group. The treatment with methimazole or pilocarpine allowed improvement of the animals in this, it became statistically significant as early as after 8 weeks of the force-feeding. This effect is quite demonstrative at 16 weeks of treatment (FIG. 7). The animals became significantly more performing compared with the placebo group and recovered a level of performance which no more significantly differs from that of the WT placebo group.

Figure 8:
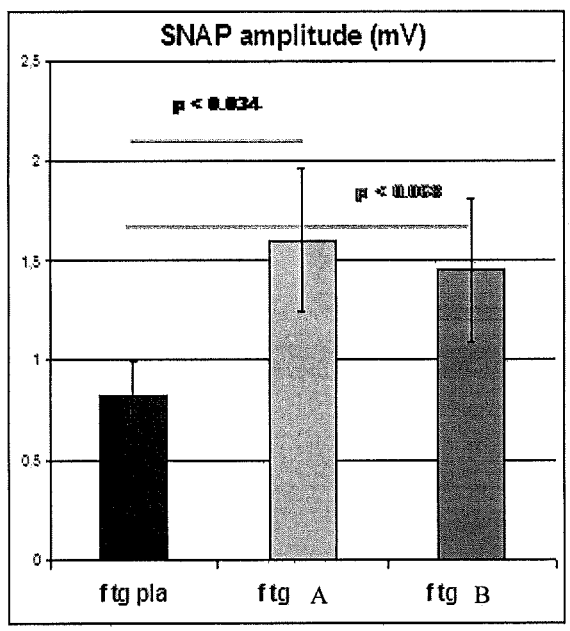
FIG. 8: Electrophysiological assessment of the sensitive nerve potential amplitude in CMT rats treated with drugs during 20 weeks. A: Methimazole; B: Pilocarpine.

The potential amplitude measured on the distal portion of the tail was found to be significantly diminished in the TG placebo group that may reflect the important axonal loss which in turn is due to the demyelination. This electrophysiological parameter turns to be significantly improved upon the treatment with methimazole (FIG. 8), while the nerve conduction velocity (NCV) was not significantly affected.

This observation allows us to suppose that the action of methimazole may prevent the axon loss, even if the myelination status of the peripheral nerves is not measurably improved. The effect of the pilocarpine seems to be essentially the same, even if because of the intra-group variability the difference with the placebo group parameter failed to reach statistical significance. In CMT1A, (sensory nerve action potential (SNAP) amplitude was more reduced and SNAP duration more prolonged than in CMT2. The reduction of composed muscle action potential (CMAP) and SNAP amplitudes in CMT1A is probably a combined effect of demyelination and axonal dysfunction.

At the end of the study morphometrical analysis has been performed. The measurement of the hindlimb tissues reveals that the sciatic nerves and soleus muscles are significantly reduced in the CMT female rats treated with placebo compared with the control WT rats. These deficiencies appear to be completely corrected by methimazole treatment: the absolute masses of the muscles and the nerves are even higher than in the control WT rats, while the entire body weight is rather diminished in the methimazole group comparatively with the placebo group (data not shown).

These data show that, in vivo, the compounds of this invention allow effective treatment of CMT. Furthermore, it should be noted that the first doses that were shown to be active for each drug is one fourth (methimazole) and one half (pilocarpine) of the dose equivalent to dosage used in human for the canonical indications.

8. Therapeutic Schema, Dosages and Routes of Administration

Below, the dosages for two combinations (that differ in administration routes) in humans are described.

(1) Compound F and Compound D

1 Administered orally as a single pharmaceutical composition: compound D from about 0.1 to about 20 mg and compound F from about 0.2 to about 50 mg every day orally for several months, the most preferred dosages for both drugs in the composition ranging from 0.1 to 5 mg per unit (per day).

2 Administered concomitantly orally for several months: compound F from about 5 to about 200 mg once a week (the most preferred dosage being up to 50 mg weekly), compound D from about 0.1 to about 20 mg daily (the most preferred dosage for this drug being from 0.1 to 5 mg per day).

3 Administered concomitantly for several months: compound D from about 0.1 to about 20 mg every day orally (the most preferred dosage for this drug being from 0.1 to 5 mg per day), and compound F as a skin patch releasing the drug preferably at a rate of about 0.2 to about 2 mg per day.

(2) Compound A and Compound F.

1 Administered chronically, orally, twice or thrice a day, as a single pharmaceutical composition in form of capsules or drops that must be dissolved in drink (preferably, in milk): the preferred total daily dosage of compound F being from about 0.1 to about 5 mg and compound A from about 1 to about 50 g.

2 Administered concomitantly for several months: compound F once a week from about 5 to about 200 mg once a week (the most preferred dosage being up to 50 mg weekly), and compound A twice a day in a drink, the total daily dosage of compound A being from about 1 to about 50 g.

3 Administered sequentially & concomitantly for long-term treatments: firstly as a single bolus of compound F (about 200 to 600 mg) orally, then in combination concomitantly: compound F as a skin patch releasing the drug** (the most preferably at a rate of about 0.2 to about 2 mg per day) and compound A twice a day during 7 days in a drink water, then no compound A during 14 days, then compound A during 7 days twice a day in a drink water (the preferred total daily dosage of compound A being from about 1 to about 50 g) etc. by intermittence.

* the dosages of this drug in any combination among those disclosed in the present invention may differ significantly in the formulations proposed for treatment of men or women.
** the same therapeutical schema as compound F & compound A (3) but instead of the skin patch a rectal/vaginal administration of low doses of compound F may be used.

BIBLIOGRAPHY

Amici S A, Dunn W A Jr, Murphy A J, Adams N C, Gale N W, Valenzuela D M, Yancopoulos G D, Notterpek L. Peripheral myelin protein 22 is in complex with alpha6beta4 integrin, and its absence alters the Schwann cell basal lamina. J Neurosci. 2006; 26(4):1179-1189.

Amici S A, Dunn W A Jr, Notterpek L. Developmental abnormalities in the nerves of peripheral myelin protein 22-deficient mice. J Neurosci Res. 2007; 85(2): 238-249.

Atanasoski S, Scherer S S, Nave K-A, Suter U. Proliferation of Schwann Cells and Regulation of Cyclin D1 Expression in an Animal Model of Charcot-Marie-Tooth Disease Type 1A. J Neurosci Res. 2002; 67(4):443-449.

Basta-Kaim A, Budziszewska B, Jaworska-Feil L, Tetich M, Leśkiewicz M, Kubera M, Lasoń W. Chlorpromazine inhibits the glucocorticoid receptor-mediated gene transcription in a calcium-dependent manner. Neuropharmacology. 2002; 43(6):1035-1043

Batty I H, Fleming I N, Downes C P. Muscarinic-receptor-mediated inhibition of insulin-like growth factor-1 receptor-stimulated phosphoinositide 3-kinase signalling in 1321N1 astrocytoma cells. Biochem J. 2004; 379(Pt 3):641-651.

Bogoyevitch M A, Ketterman A J, Sugden P H. Cellular stresses differentially activate c-Jun N-terminal protein kinases and extracellular signal-regulated protein kinases in cultured ventricular myocytes. J Biol Chem. 1995; 270(50):29710-29717.

Brancolini C, Marzinotto S, Edomi P, Agostoni E, Fiorentini C, Müller H W, Schneider C. Rho-dependent regulation of cell spreading by the tetraspan membrane protein Gas3/PMP22. Mol. Biol. Cell 1999; 10: 2441-2459.

Castellone M D, Teramoto H, Gutkind J S. Cyclooxygenase-2 and Colorectal Cancer Chemoprevention: The β-Catenin Connection. Cancer Res. 2006; 66(23):11085-11088.

Chen X R, Besson V C, Palmier B, Garcia Y, Plotkine M, Marchand-Leroux C. Neurological recovery-promoting, anti-inflammatory, and anti-oxidative effects afforded by fenofibrate, a PPAR alpha agonist, in traumatic brain injury. J Neurotrauma 2007; 24 (7): 1119-1131.

Chies R, Nobbio L, Edomi P, Schenone A, Schneider C, Brancolini C. Alterations in the Arf6-regulated plasma membrane endosomal recycling pathway in cells overexpressing the tetraspan protein Gas3/PMP22. J Cell Sci. 2003; 116(Pt 6): 987-999.

Constable A L, Armati P J. DMSO induction of the leukotriene LTC4 by Lewis rat Schwann cells. J Neurol Sci 1999; 162(2): 120-126.

Devaux J J, Scherer S S. Altered ion channels in an animal model of Charcot-Marie-Tooth disease type IA. J Neurosci. 2005; 25(6): 1470-1480.

Diep Q N, Benkirane K, Amiri F, Cohn J S, Endemann D, Schiffrin E L. PPAR alpha activator fenofibrate inhibits myocardial inflammation and fibrosis in angiotensin II-infused rats. J Mol Cell Cardiol. 2004; 36 (2): 295-304.

Dracheva S, Davis K L, Chin B, Woo D A, Schmeidler J, Haroutunian V. Myelin-associated mRNA and protein expression deficits in the anterior cingulate cortex and hippocampus in elderly schizophrenia patients. Neurobiol Dis. 2006 March; 21(3):531-540.

D'Urso D, Ehrhardt P, Müller H W. Peripheral myelin protein 22 and protein zero: a novel association in peripheral nervous system myelin. J Neurosci. 1999; 19(9): 3396-3403.

Fortun J, Dunn W A Jr, Joy S, Li J, Notterpek L. Emerging role for autophagy in the removal of aggresomes in Schwann cells. J Neurosci. 2003; 23(33): 10672-10680.

Fortun J, Li J, Go J, Fenstermaker A, Fletcher B S, Notterpek L. Impaired proteasome activity and accumulation of ubiquitinated substrates in a hereditary neuropathy model. J Neurochem 2005; 92:1531-1541.

Fortun J, Go J C, Li J, Amici S A, Dunn W A Jr, Notterpek L. Alterations in degradative pathways and protein aggregation in a neuropathy model based on PMP22 overexpression. Neurobiol Dis. 2006; 22(1):153-164.

Fortun J, Verrier J D, Go J C, Madorsky I, Dunn W A, Notterpek L. The formation of peripheral myelin protein 22 aggregates is hindered by the enhancement of autophagy and expression of cytoplasmic chaperones. Neurobiol Dis. 2007; 25(2): 252-265.

Galvez A S, Ulloa J A, Chiong M, Criollo A, Eisner V, Barros L F, Lavandero S. Aldose reductase induced by hyperosmotic stress mediates cardiomyocyte apoptosis: differential effects of sorbitol and mannitol. J Biol Chem. 2003; 278(40):38484-38494.

Groyer G, Eychenne B, Girard C, Rajkowski K, Schumacher M, Cadepond F. Expression and functional state of the corticosteroid receptors and 11 beta-hydroxysteroid dehydrogenase type 2 in Schwann cells. Endocrinology. 2006; 147(9):4339-4350.

Kantamneni S, Corrêa S A, Hodgkinson G K, Meyer G, Vinh N N, Henley J M, Nishimune A. GISP: a novel brain-specific protein that promotes surface expression and function of GABA(B) receptors. J Neurochem. 2007; 100(4):1003-17.

Khajavi M, Shiga K, Wiszniewski W, He F, Shaw C A, Yan J, Wensel T G, Snipes G J, Lupski J R. Oral curcumin mitigates the clinical and neuropathologic phenotype of the Trembler-J mouse: a potential therapy for inherited neuropathy. Am J Hum Genet. 2007; 81(3): 438-453.

Kobsar I, Hasenpusch-Theil K, Wessig C, Müller H W, Martini R. Evidence for Macrophage-Mediated Myelin Disruption in an Animal Model for Charcot-Marie-Tooth Neuropathy Type 1A. J. Neurosci Res 2005; 81:857-864.

Lange C A, Shen T et al. Phosphorylation of human progesterone receptors at serine-294 by mitogen-activated protein kinase signals their degradation by the 26S proteasome. PNAS USA. 2000; 97: 1032-1037.

Le-Niculescu H, Kurian S M, Yehyawi N, Dike C, Patel S D, Edenberg H J, Tsuang M T, Salomon D R, Nurnberger J I Jr, Niculescu A B. Identifying blood biomarkers for mood disorders using convergent functional genomics. Mol Psychiatry. 2008 Feb. 26. [Epub ahead of print].

Li W W, Le Goascogne C, Ramaugé M, Schumacher M, Pierre M, Courtin F. Induction of type 3 iodothyronine deiodinase by nerve injury in the rat peripheral nervous system. Endocrinology. 2001; 142(12):5190-5197.

Lupski J R, Wise C A, Kuwano. A, Pentao L, Parke J T, Glaze D G, Ledbetter D H, Greenberg F, Patel P I. Gene dosage is a mechanism for Charcot-Marie-Tooth disease type 1A. Nat Genet. 1992; 1(1): 29-33.

Mäurer M, Kobsar I, Berghoff M, Schmid C D, Carenini S, Martini R. Role of immune cells in animal models for inherited neuropathies: facts and visions. J Anat. 2002; 200(4): 405-414.

Melcangi R C, Cavarretta I T, Ballabio M, Leonelli E, Schenone A, Azcoitia I, Miguel Garcia-Segura L, Magnaghi V. Peripheral nerves: a target for the action of neuroactive steroids. Brain Res Rev. 2005; 48(2): 328-338.

Mercier G, Turque N, Schumacher M. Rapid effects of triiodothyronine on immediate-early gene expression in Schwann cells. Glia. 2001; 35(2):81-89.

Meyer Zu Horste G., Nave K-A. Animal models of inherited neuropathies. Curr. Opin. Neurol. 2006; 19(5): 464-473.

Meyer zu Horste G, Prukop T, Liebetanz D, Mobius W, Nave K A, Sereda M W. Antiprogesterone therapy uncouples axonal loss from demyelination in a transgenic rat model of CMT1A neuropathy. Ann Neurol. 2007; 61 (1): 61-72.

Miller A L, Garza A S, Johnson B H, Thompson E B. Pathway interactions between MAPKs, mTOR, PKA, and the glucocorticoid receptor in lymphoid cells. Cancer Cell Int. 2007; 28:7:3

Muja N, Blackman S C, Le Breton G C, DeVries G H. Identification and functional characterization of thromboxane A2 receptors in Schwann cells. J Neurochem. 2001; 78(3):446-456.

Muller D L, Unterwald E M. In Vivo Regulation of Extracellular Signal-Regulated Protein Kinase (ERK) and Protein Kinase B (Akt) Phosphorylation by Acute and Chronic Morphine. JPET 2004; 310:774-782.

Nambu H, Kubo E, Takamura Y, Tsuzuki S, Tamura M, Akagi Y. Attenuation of aldose reductase gene suppresses high-glucose-induced apoptosis and oxidative stress in rat lens epithelial cells. Diabetes Res Clin Pract. 2008; 82(1): 18-24.

Nave K A, Sereda M W, Ehrenreich H. Mechanisms of disease: inherited demyelinating neuropathies—from basic to clinical research. Nat Clin Pract Neurol. 2007; 3(8): 453-464.

Niemann S., Sereda M. W., Rossner M., Stewart H., Suter U., Meinck H. M., Griffiths I. R., Nave K-A. The "CMT rat": peripheral neuropathy and dysmyelination caused by transgenic overexpression of PMP22. Ann. N.-Y. Acad. Sci. 1999; 883:254-261.

Notterpek L, Shooter E M, Snipes G J. Upregulation of the endosomal-lysosomal pathway in the trembler-J neuropathy. J Neurosci. 1997; 17(11): 4190-4200.

Obrietan K, van den Pol A N. GABAB receptor-mediated inhibition of GABAA receptor calcium elevations in developing hypothalamic neurons. J Neurophysiol. 1998; 79(3):1360-1370.

Ogata T, Iijima S, Hoshikawa S, Miura T, Yamamoto S, Oda H, Nakamura K, Tanaka S Opposing extracellular signal-regulated kinase and Akt pathways control Schwann cell myelination. J Neurosci. 2004; 24(30):6724-6732.

Ohsawa Y, Murakami T, Miyazaki Y, Shirabe T, Sunada Y. Peripheral myelin protein 22 is expressed in human central nervous system. J Neurol Sci. 2006; 247(1):11-15.

Passage E, Norreel J C, Noack-Fraissignes P, Sanguedolce V, Pizant J, Thirion X, Robaglia-Schlupp A, Pellissier J F, Fontes M. Ascorbic acid treatment corrects the phenotype of a mouse model of Charcot-Marie-Tooth disease. Nature Med. 2004; 10(4): 396-401.

Perea J, Robertson A, Tolmachova T, Muddle I, King R H, Ponsford S, Thomas P K, Huxley C. Induced myelination and demyelination in a conditional mouse model of Charcot-Marie-Tooth disease type 1A. Hum Mol Genet. 2001; 10(10):1007-1018.

Roa B B, Garcia C A, Suter U, Kulpa D A, Wise C A, Mueller J, Welcher A A, Snipes G J, Shooter E M, Patel P I, Lupski J R. Charcot-Marie-Tooth disease type 1A. Association with a spontaneous point mutation in the PMP22 gene. N Engl J Med. 1993; 329(2): 96-101.

Robaglia-Schlupp A, Pizant J, Norreel J C, Passage E, Saberan-Djoneidi D, Ansaldi J L, Vinay L, Figarella-Branger D, Levy N, Clarac F, Cau P, Pellissier J F, Fontes M. PMP22 overexpression causes dysmyelination in mice. Brain 2002; 125(Pt 10): 2213-2221.

Robert F, Guennoun R, Desarnaud F, Do-Thi A, Benmessahel Y, Baulieu E E, Schumacher M. Synthesis of progesterone in Schwann cells: regulation by sensory neurons. Eur J Neurosci. 2001; 13(5): 916-924.

Roux K J, Amici S A, Notterpek L. The temporospatial expression of peripheral myelin protein 22 at the developing blood-nerve and blood-brain barriers. J Comp Neurol. 2004; 474(4):578-588.

Sancho S, Young P, Suter U. Regulation of Schwann cell proliferation and apoptosis in PMP22-deficient mice and mouse models of Charcot-Marie-Tooth disease type 1A. Brain 2001; 124(Pt 11): 2177-2187.

Schumacher M, Guennoun R, Mercier G, Désarnaud F, Lacor P, Bénavides J, Ferzaz B, Robert F, Baulieu E E. Progesterone synthesis and myelin formation in peripheral nerves. Brain Res Rev. 2001; 37(1-3): 343-359.

Sereda M W, Meyer zu Horste G, Suter U, et al. Therapeutic administration of progesterone antagonist in a model of Charcot-Marie-Tooth disease (CMT-1A). Nat Med 2003; 9: 1533-1537.

Sereda M W, Nave K A. Animal models of Charcot-Marie-Tooth disease type 1A (CMT1A). Neuromol Med 2006; 8: 205-215.

Stirnweiss J, Valkova C, Ziesché E, Drube S, Liebmann C. Muscarinic M2 receptors mediate transactivation of EGF receptor through Fyn kinase and without matrix metalloproteases. Cell Signal. 2006; 18(8):1338-1349.

Suter U, Scherer S S. Disease mechanisms in inherited neuropathies. Nat. Rev. Neurosci. 2003; 4: 714-726.

Suter U, Welcher A A, Ozcelik T, Snipes G J, Kosaras B, Francke U, Billings-Gagliardi S, Sidman R L, Shooter E M. Trembler mouse carries a point mutation in a myelin gene. Nature. 1992; 356(6366): 241-244.

Thomas P K, Marques W Jr, Davis M B, Sweeney M G, King R H, Bradley J L, Muddle J R, Tyson J, Malcolm S, Harding A E. The phenotypic manifestations of chromosome 17p11.2 duplication. Brain 1997; 120 (Pt 3): 465-478.

Tobler A R, Liu N, Mueller L, Shooter E M. Differential aggregation of the Trembler and Trembler J mutants of peripheral myelin protein 22. PNAS USA. 2002; 99(1): 483-488.

Tu H, Rondard P, Xu C, Bertaso F, Cao F, Zhang X, Pin J P, Liu J. Dominant role of GABAB2 and Gbetagamma for GABAB receptor-mediated-ERK1/2/CREB pathway in cerebellar neurons. Cell Signal. 2007; 19(9):1996-2002.

Uht R M, Anderson C M, Webb P, Kushner P J. Transcriptional activities of estrogen and glucocorticoid receptors are functionally integrated at the AP-1 response element. Endocrinology. 1997 July; 138(7):2900-2908.

Ulzheimer J C, Peles E, Levinson S R, Martini R. Altered expression of ion channel isoforms at the node of Ranvier in P0-deficient myelin mutants. Mol Cell Neurosci. 2004; 25(1): 83-94.

Vallat J M, Sindou P, Preux P M, Tabaraud F, Milor A M, Couratier P, LeGuern E, Brice A. Ultrastructural PMP22 expression in inherited demyelinating neuropathies. Ann Neurol. 1996; 39(6): 813-817.

Walter I B. Nuclear triiodothyronine receptor expression is regulated by axon-Schwann cell contact. Neuroreport. 1993; 5(2):137-140.

Walter I B, Deruaz J P, de Tribolet N. Differential expression of triiodothyronine receptors in schwannoma and neurofibroma: role of Schwann cell-axon interaction. Acta Neuropathol (Berl). 1995; 90(2):142-149.

Welch W J, Brown C R. Influence of molecular and chemical chaperones on protein folding. Cell Stress Chaperones. 1996; 1(2):109-115.

Woodhams P L, MacDonald R E, Collins S D, Chessell I P, Day N C. Localisation and modulation of prostanoid receptors EP1 and EP4 in the rat chronic constriction injury model of neuropathic pain. Eur J Pain. 2007; 11(6):605-613.

We claim:

1. A method for treating Charcot-Marie-Tooth (CMT) disease of type 1 A (CMT1A), comprising administering to a subject in need thereof an effective amount of D-sorbitol, or a salt thereof or a sustained release formulation thereof.

2. The method of claim 1, wherein D-sorbitol or a salt thereof is administered at a daily dose of about 1 to about 50 g.

3. The method of claim 1, wherein D-sorbitol, or a salt thereof or a sustained release formulation thereof, is administered orally.

4. The method of claim 1, wherein D-sorbitol, or a salt thereof or a sustained release formulation thereof, is formulated in a unit dosage form.

5. The method of claim 1, wherein pmp22 expression in Schwann cells of the subject is reduced.

6. The method of claim 1, wherein the strength or motor performance of the subject is improved.

7. The method of claim 1, wherein D-sorbitol or a salt thereof is administered orally in a unit dosage form at a daily dose of about 1 to about 50 g.

8. The method of claim 1, comprising administering to the subject an effective amount of D-sorbitol or a salt thereof, optionally in combination with an excipient, wherein none of the following is administered to the subject: baclofen; naltrexone; pilocarpine; methimazole; mifepristone; or ketoprofen; or a salt thereof or prodrug thereof.

9. The method of claim 8, wherein D-sorbitol is administered orally in a unit dosage form at a daily dose of 1 to 50 g.

* * * * *